(12) United States Patent
Miller et al.

(10) Patent No.: US 8,137,953 B2
(45) Date of Patent: Mar. 20, 2012

(54) LACTIC ACID-PRODUCING YEAST CELLS HAVING NONFUNCTIONAL L- OR D-LACTATE:FERRICYTOCHROME C OXIDOREDUCTASE CELLS

(75) Inventors: Matthew Miller, Boston, MA (US); Pirkko Suominen, Maple Grove, MN (US); Aristos Aristidou, Highland Ranch, CO (US); Benjamin Matthew Hause, Currie, MN (US); Pim Van Hoek, Camarillo, CA (US); Catherine Asleson Dundon, Minneapolis, MN (US)

(73) Assignee: Cargill Inc., Wayzata, MN (US)

( * ) Notice: Subject to any disclaimer, the term of this patent is extended or adjusted under 35 U.S.C. 154(b) by 824 days.

(21) Appl. No.: 12/093,757

(22) PCT Filed: Nov. 17, 2006

(86) PCT No.: PCT/US2006/044815
§ 371 (c)(1),
(2), (4) Date: Jul. 15, 2008

(87) PCT Pub. No.: WO2007/117282
PCT Pub. Date: Oct. 18, 2007

(65) Prior Publication Data
US 2009/0253189 A1 Oct. 8, 2009

Related U.S. Application Data

(60) Provisional application No. 60/739,458, filed on Nov. 23, 2005, provisional application No. 60/739,824, filed on Nov. 23, 2005.

(51) Int. Cl.
*C12N 1/19* (2006.01)
*C12N 1/00* (2006.01)
*C12N 15/70* (2006.01)
*C12Q 1/68* (2006.01)

(52) U.S. Cl. ............ 435/254.2; 435/1; 435/6; 435/254; 435/471

(58) Field of Classification Search ................. None
See application file for complete search history.

(56) References Cited

U.S. PATENT DOCUMENTS

| | | |
|---|---|---|
| 6,429,006 B1 | 8/2002 | Porro |
| 6,485,947 B1 | 11/2002 | Rajgarhia |
| 7,049,108 B2 | 5/2006 | Porro |
| 7,109,010 B2 | 9/2006 | Rajgarhia |
| 7,141,410 B2 | 11/2006 | Rajgarhia |
| 7,229,805 B2 | 6/2007 | Rajgarhia |

FOREIGN PATENT DOCUMENTS

| | | | |
|---|---|---|---|
| WO | WO 99/14335 | * | 3/1999 |
| WO | WO 02/42471 | | 5/2002 |
| WO | WO 03/049525 | | 6/2003 |

OTHER PUBLICATIONS

Ishida et al., "Efficient production of L-Lactic Acid by metabolically engineered *Saccharomyces cerevisiae* with a genome-integrated L-lactate dehydrogenase gene", Applied and Environmental Microbiology 71(4): 1964-1970 (Apr. 2005)).*
Guiard, "Structure, expresion and regulation of a nuclear gene encoding a mitrochondrial protein . . . ", EMBO Journal, 4 (1985), 3265-3272.
Ishida et al., "Efficient Production of L-Lactic Acid by Metabolically Engineered . . . ", Appl. and Environmental Microbiol. 71 (2005), pp. 1964-1970.

* cited by examiner

*Primary Examiner* — Anand Desai
(74) *Attorney, Agent, or Firm* — Gary C Cohn PLLC

(57) ABSTRACT

Yeast cells having an exogenous lactate dehydrogenase gene ae modified by reducing L- or D-lactate:ferricytochrome c oxidoreductase activity in the cell. This leads to reduced consumption of lactate by the cell and can increase overall lactate yields in a fermentation process. Cells having the reduced L- or D-lactate:ferricytochrome c oxidoreductase activity can be screened for by resistance to organic acids such as lactic or glycolic acid.

7 Claims, 15 Drawing Sheets

Figure 1:
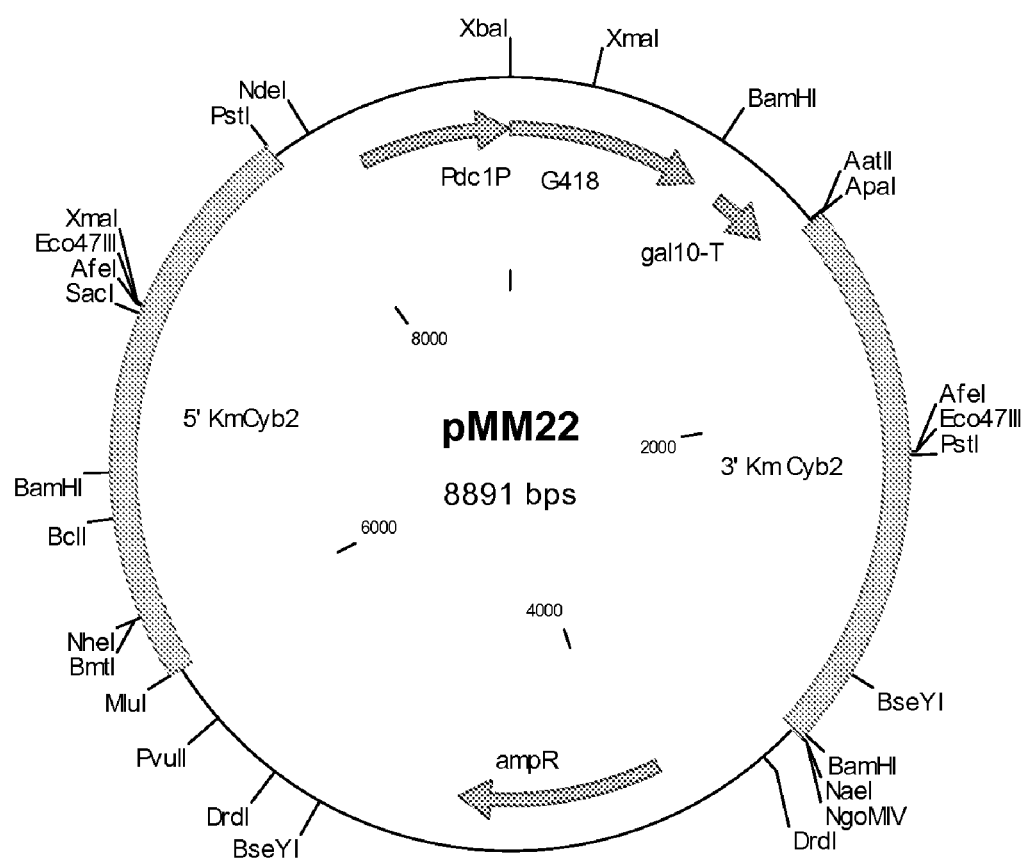

SEQUENCE LISTING

```
<160> NUMBER OF SEQ ID NOS: 90

<210> SEQ ID NO 1
<211> LENGTH: 1779
<212> TYPE: DNA
<213> ORGANISM: Kluyveromyces marxianus
```

<400> SEQUENCE: 1

```
atgagatctg cagctagagt catcaacaag agctgtagcg gctctgctct ttcgagaaga      60
tgtctgagaa aatcgagctt gagcatgagt atgagatatt taagtacttc gaacatcgga     120
gtcagaaaag gtttcaacgg acagggtaaa agttcgaata aaacgatgtt gttttggct     180
gctgggctt cagctgtagc tgggatcggg ctgctctctc aatttagcga cagcttgcaa     240
aatgctacga agaagagct aaacaagcca aaggtttccc cgctcgaggt cgccaagcac      300
tcgagtcccg atgactgctg gtggtgatc gatgggtttg tctacaattt gacggaattc      360
attagcgccc atcctggtgg accagctatc atcgagaaca acgccggtaa ggatgtgacg     420
gcgatctttg cccaattca tgcgccagat gtcattgaga agtacattgc tccggagaac      480
cggatcggtc ctctagacgg aaaatgccc gacgacttga tctgtgcgcc attgacgccc     540
ggtgagactc ctgaggatgt tgccagaaaa gaggagttgc gtcaaaatat gccagatctc     600
gactcgttgg tcaacattta cgatttcgag ttcttggcgt cccagatttt gaccaaacag     660
gcatggtcct actactcttc tgctgccgat gacgaagtca cccacagaga gaaccatgct     720
gcataccacc gtatcttctt caagccaaga atcctagtca acgtcaagga ggtggacact     780
tccaccacca tgttgggtga aaaagtgggt gttccattct atgtgtctgc taccgctttta    840
tgtaaattgg gtaatccaaa ggaaggtgaa aaggatatcg ctagaggttg tggcgagagc    900
gacgtgaagc caatccagat gatttccact ttggcctctt gttctttgca gaaaatcgtc    960
gaagcagcac cttccaagga ccaaatccaa tggttccaat gtatgtcaa cagtgaccgt    1020
aagattaccg aggaattgat caaaaacgtc gaaaagctgg gcttgaaggc tatcttcgtt    1080
actgtggatg cccatctct cggtaacaga gaaaaggatg ctaaggtcaa attcaccaac    1140
aaggacagtt ccgcaaaggc catggaaaag agcaacgtca aggaatccaa gggtgcttcc    1200
agagctcttt ccactttcat tgaccctgct ctatgctggg atgatatcgt taccttgaaa    1260
tcaaagacca agttgccaat tgtcattaag ggtgttcaat gcgtcgaaga cgtcttgaaa    1320
gccgcagaaa ttggtgccgc cggtgtcgtc ttgtccaacc acggtggtag acaactagac    1380
tttccagag cgccaatcga agtcttggcc gaaacaatgc ctattctaaa agaaaagaaa    1440
ctagacgaca agatcgaaat cttcatcgat ggtggtgtca agaagggtac cgatataattg   1500
aaggccttgt gtcttggtgc caagggtgtc ggtttaggta gaccattctt gtacgcaaac    1560
agttgttacg gtaaggaagg tgtcaagaaa gctatcgaat gctaaagga cgaactagaa    1620
atgtcaatga gattgcttgg tgtcactagc atcgaccaat tgtctgagaa gtatctggat    1680
ctatctactc ttcacggtag aactgttagc gtacctcgtg acaacttgta caacggagtg    1740
tatgttccac acgaaccaac tgacttcaag gaaaattga                            1779
```

<210> SEQ ID NO 2
<211> LENGTH: 592
<212> TYPE: PRT
<213> ORGANISM: Kluyveromyces marxianus

<400> SEQUENCE: 2

```
Met Arg Ser Ala Ala Arg Val Ile Asn Lys Ser Cys Ser Gly Ser Ala
1               5                  10                  15

Leu Ser Arg Arg Cys Leu Arg Lys Ser Ser Leu Ser Met Ser Met Arg
            20                  25                  30

Tyr Leu Ser Thr Ser Asn Ile Gly Val Arg Lys Gly Phe Asn Gly Gln
        35                  40                  45
```

```
Gly Lys Ser Ser Asn Lys Thr Met Leu Phe Leu Ala Ala Gly Ala Ser
 50                  55                  60

Ala Val Ala Gly Ile Gly Leu Leu Ser Gln Phe Ser Asp Ser Leu Gln
 65                  70                  75                  80

Asn Ala Thr Lys Glu Glu Leu Asn Lys Pro Lys Val Ser Pro Leu Glu
                 85                  90                  95

Val Ala Lys His Ser Ser Pro Asp Asp Cys Trp Val Val Ile Asp Gly
             100                 105                 110

Phe Val Tyr Asn Leu Thr Glu Phe Ile Ser Ala His Pro Gly Gly Pro
         115                 120                 125

Ala Ile Ile Glu Asn Asn Ala Gly Lys Asp Val Thr Ala Ile Phe Gly
130                 135                 140

Pro Ile His Ala Pro Asp Val Ile Glu Lys Tyr Ile Ala Pro Glu Asn
145                 150                 155                 160

Arg Ile Gly Pro Leu Asp Gly Lys Met Pro Asp Asp Leu Ile Cys Ala
                165                 170                 175

Pro Leu Thr Pro Gly Glu Thr Pro Glu Asp Val Ala Arg Lys Glu Glu
            180                 185                 190

Leu Arg Gln Asn Met Pro Asp Leu Asp Ser Leu Val Asn Ile Tyr Asp
        195                 200                 205

Phe Glu Phe Leu Ala Ser Gln Ile Leu Thr Lys Gln Ala Trp Ser Tyr
210                 215                 220

Tyr Ser Ser Ala Ala Asp Asp Glu Val Thr His Arg Glu Asn His Ala
225                 230                 235                 240

Ala Tyr His Arg Ile Phe Phe Lys Pro Arg Ile Leu Val Asn Val Lys
                245                 250                 255

Glu Val Asp Thr Ser Thr Thr Met Leu Gly Glu Lys Val Gly Val Pro
            260                 265                 270

Phe Tyr Val Ser Ala Thr Ala Leu Cys Lys Leu Gly Asn Pro Lys Glu
        275                 280                 285

Gly Glu Lys Asp Ile Ala Arg Gly Cys Gly Glu Ser Asp Val Lys Pro
290                 295                 300

Ile Gln Met Ile Ser Thr Leu Ala Ser Cys Ser Leu Gln Glu Ile Val
305                 310                 315                 320

Glu Ala Ala Pro Ser Lys Asp Gln Ile Gln Trp Phe Gln Leu Tyr Val
                325                 330                 335

Asn Ser Asp Arg Lys Ile Thr Glu Glu Leu Ile Lys Asn Val Glu Lys
            340                 345                 350

Leu Gly Leu Lys Ala Ile Phe Val Thr Val Asp Ala Pro Ser Leu Gly
        355                 360                 365

Asn Arg Glu Lys Asp Ala Lys Val Lys Phe Thr Asn Lys Asp Ser Ser
370                 375                 380

Ala Lys Ala Met Glu Lys Ser Asn Val Lys Glu Ser Lys Gly Ala Ser
385                 390                 395                 400

Arg Ala Leu Ser Thr Phe Ile Asp Pro Ala Leu Cys Trp Asp Asp Ile
                405                 410                 415

Val Thr Leu Lys Ser Lys Thr Lys Leu Pro Ile Val Ile Lys Gly Val
            420                 425                 430

Gln Cys Val Glu Asp Val Leu Lys Ala Ala Glu Ile Gly Ala Ala Gly
        435                 440                 445

Val Val Leu Ser Asn His Gly Gly Arg Gln Leu Asp Phe Ser Arg Ala
450                 455                 460

Pro Ile Glu Val Leu Ala Glu Thr Met Pro Ile Leu Lys Glu Lys Lys
465                 470                 475                 480
```

-continued

Leu Asp Asp Lys Ile Glu Ile Phe Ile Asp Gly Gly Val Arg Arg Gly
                485                 490                 495

Thr Asp Ile Leu Lys Ala Leu Cys Leu Gly Ala Lys Gly Val Gly Leu
            500                 505                 510

Gly Arg Pro Phe Leu Tyr Ala Asn Ser Cys Tyr Gly Lys Glu Gly Val
                515                 520                 525

Lys Lys Ala Ile Glu Leu Leu Lys Asp Glu Leu Glu Met Ser Met Arg
            530                 535                 540

Leu Leu Gly Val Thr Ser Ile Asp Gln Leu Ser Glu Lys Tyr Leu Asp
545                 550                 555                 560

Leu Ser Thr Leu His Gly Arg Thr Val Ser Val Pro Arg Asp Asn Leu
                565                 570                 575

Tyr Asn Gly Val Tyr Val Pro His Glu Pro Thr Asp Phe Lys Glu Asn
            580                 585                 590

<210> SEQ ID NO 3
<211> LENGTH: 33
<212> TYPE: DNA
<213> ORGANISM: Artificial
<220> FEATURE:
<223> OTHER INFORMATION: Primer

<400> SEQUENCE: 3
cagataacgc gtctggctcg atacttctta ttc                                33

<210> SEQ ID NO 4
<211> LENGTH: 33
<212> TYPE: DNA
<213> ORGANISM: Artificial
<220> FEATURE:
<223> OTHER INFORMATION: Primer

<400> SEQUENCE: 4
tgcagactgc agtgctactg gtattgtatt act                                33

<210> SEQ ID NO 5
<211> LENGTH: 34
<212> TYPE: DNA
<213> ORGANISM: Artificial
<220> FEATURE:
<223> OTHER INFORMATION: Primer

<400> SEQUENCE: 5
attatagggc cccacaaaat gtatctatct ctcc                               34

<210> SEQ ID NO 6
<211> LENGTH: 34
<212> TYPE: DNA
<213> ORGANISM: Artificial
<220> FEATURE:
<223> OTHER INFORMATION: Primer

<400> SEQUENCE: 6
tataatgccg gccagaagtc tctggatcct cttc                               34

<210> SEQ ID NO 7
<211> LENGTH: 20
<212> TYPE: DNA
<213> ORGANISM: Artificial
<220> FEATURE:
<223> OTHER INFORMATION: Primer

<400> SEQUENCE: 7

```
cctgaccact aaacgtctac                                                  20
```

<210> SEQ ID NO 8
<211> LENGTH: 20
<212> TYPE: DNA
<213> ORGANISM: Artificial
<220> FEATURE:
<223> OTHER INFORMATION: Primer

<400> SEQUENCE: 8

```
cacctctttg catgagcttg                                                  20
```

<210> SEQ ID NO 9
<211> LENGTH: 20
<212> TYPE: DNA
<213> ORGANISM: Artificial
<220> FEATURE:
<223> OTHER INFORMATION: Primer

<400> SEQUENCE: 9

```
ctggatctac agcgattctc                                                  20
```

<210> SEQ ID NO 10
<211> LENGTH: 20
<212> TYPE: DNA
<213> ORGANISM: Artificial
<220> FEATURE:
<223> OTHER INFORMATION: Primer

<400> SEQUENCE: 10

```
tgtaccggct gtccttaaac                                                  20
```

<210> SEQ ID NO 11
<211> LENGTH: 32
<212> TYPE: DNA
<213> ORGANISM: Artificial
<220> FEATURE:
<223> OTHER INFORMATION: Primer

<400> SEQUENCE: 11

```
tccccggtcg accggaactt agcttactcg tc                                    32
```

<210> SEQ ID NO 12
<211> LENGTH: 32
<212> TYPE: DNA
<213> ORGANISM: Artificial
<220> FEATURE:
<223> OTHER INFORMATION: Primer

<400> SEQUENCE: 12

```
ttgcgaggat cctgagtgca gtagctgtac ac                                    32
```

<210> SEQ ID NO 13
<211> LENGTH: 706
<212> TYPE: DNA
<213> ORGANISM: Kluyveromyces marxianus

<400> SEQUENCE: 13

```
cactcgcaag ctgtgccatc gcccaacggt taattataag aaatcaacat cagccaacaa      60 ctatttcgt  cccctctttt tcagtggtaa cgagcaatta cattagtaag agactatttt     120
cttcagtgat tgtaattttt ttttcagtga tttgtaattc tttctcgaaa tatgcgggct     180
waamtaatcc ggacattcac tacatgcaag gaaaaacgag aaccgcggag atttcctcag     240
taagtaacaa tgatgatctt tttacgcttc atcatcactt tccaaagttc taagctataa     300
```

```
gttcaagcct agatacgctg aaaaactcct gaccaacaat gtaaagaaaa caattacaat    360
tgtaaggttg aaaacatcta aaaatgaaat attttattgt acatgcacac cctgatagtc    420
attctcttac ttcatccctg aaagacgtgg ctgtacaaga gttggaatcg caaggtcatg    480
aggttaaagt tagtgatctt tatgctcaaa agtggaaggc ctcaatagac cgtgacgacw    540
wmaaaaaama aamrmaagaa gagaggttaa aaataccccca agcttcttat gaagcgtatg    600
ccagaggagc attaacaaaa gacgtaaatc aggaacagga aaaacttatt tgggcggact    660
ttgtcatttt gtcgtttcct atatggtggt cttctatgcc ggctag                   706
```

<210> SEQ ID NO 14
<211> LENGTH: 30
<212> TYPE: DNA
<213> ORGANISM: Artificial
<220> FEATURE:
<223> OTHER INFORMATION: Primer

<400> SEQUENCE: 14

```
tgtcagcatg cactcgcaag ctgtgccatc                                      30
```

<210> SEQ ID NO 15
<211> LENGTH: 33
<212> TYPE: DNA
<213> ORGANISM: Artificial
<220> FEATURE:
<223> OTHER INFORMATION: Primer

<400> SEQUENCE: 15

```
aaccttgtcg actagccggc atagaagacc acc                                  33
```

<210> SEQ ID NO 16
<211> LENGTH: 30
<212> TYPE: DNA
<213> ORGANISM: Artificial
<220> FEATURE:
<223> OTHER INFORMATION: Primer

<400> SEQUENCE: 16

```
tgtcaggatc cactcgcaag ctgtgccatc                                      30
```

<210> SEQ ID NO 17
<211> LENGTH: 33
<212> TYPE: DNA
<213> ORGANISM: Artificial
<220> FEATURE:
<223> OTHER INFORMATION: Primer

<400> SEQUENCE: 17

```
aaccttcccg ggtagccggc atagaagacc acc                                  33
```

<210> SEQ ID NO 18
<211> LENGTH: 33
<212> TYPE: DNA
<213> ORGANISM: Artificial
<220> FEATURE:
<223> OTHER INFORMATION: Primer

<400> SEQUENCE: 18

```
aaaaaagtcg accgataaca agctcatgca aag                                  33
```

<210> SEQ ID NO 19
<211> LENGTH: 32
<212> TYPE: DNA
<213> ORGANISM: Artificial
<220> FEATURE:

<223> OTHER INFORMATION: Primer

<400> SEQUENCE: 19
aaaaaaagat ctgcgtaacg aaataaatcc gc                            32

<210> SEQ ID NO 20
<211> LENGTH: 32
<212> TYPE: DNA
<213> ORGANISM: Artificial
<220> FEATURE:
<223> OTHER INFORMATION: Primer

<400> SEQUENCE: 20
aaaaaacccg ggcttcctcc gctgcaggtt ca                            32

<210> SEQ ID NO 21
<211> LENGTH: 32
<212> TYPE: DNA
<213> ORGANISM: Artificial
<220> FEATURE:
<223> OTHER INFORMATION: Primer

<400> SEQUENCE: 21
aaaaaagagc tcgaagtctc tggatcctct tc                            32

<210> SEQ ID NO 22
<211> LENGTH: 33
<212> TYPE: DNA
<213> ORGANISM: Artificial
<220> FEATURE:
<223> OTHER INFORMATION: Primer

<400> SEQUENCE: 22
aaaaaagacg tcctggctcg atacttctta ttc                           33

<210> SEQ ID NO 23
<211> LENGTH: 32
<212> TYPE: DNA
<213> ORGANISM: Artificial
<220> FEATURE:
<223> OTHER INFORMATION: Primer

<400> SEQUENCE: 23
aaaaaaggcg ccgctggcag atactagttc ag                            32

<210> SEQ ID NO 24
<211> LENGTH: 20
<212> TYPE: DNA
<213> ORGANISM: Artificial
<220> FEATURE:
<223> OTHER INFORMATION: Primer

<400> SEQUENCE: 24
cgctgtgctg tgcactgtaa                                          20

<210> SEQ ID NO 25
<211> LENGTH: 32
<212> TYPE: DNA
<213> ORGANISM: Artificial
<220> FEATURE:
<223> OTHER INFORMATION: Primer

<400> SEQUENCE: 25
aaaaaagagc tcgaagtctc tggatcctct tc                            32

<210> SEQ ID NO 26

```
<211> LENGTH: 32
<212> TYPE: DNA
<213> ORGANISM: Artificial
<220> FEATURE:
<223> OTHER INFORMATION: Primer

<400> SEQUENCE: 26
aaaaaaggta ccctgcaatc acccaacgga at                                     32

<210> SEQ ID NO 27
<211> LENGTH: 32
<212> TYPE: DNA
<213> ORGANISM: Artificial
<220> FEATURE:
<223> OTHER INFORMATION: Primer

<400> SEQUENCE: 27
aaaaaatcta gataatgtta cttctcttgg ag                                     32

<210> SEQ ID NO 28
<211> LENGTH: 32
<212> TYPE: DNA
<213> ORGANISM: Artificial
<220> FEATURE:
<223> OTHER INFORMATION: Primer

<400> SEQUENCE: 28
aaaaaacccg gggagaggga gaggataaag ag                                     32

<210> SEQ ID NO 29
<211> LENGTH: 32
<212> TYPE: DNA
<213> ORGANISM: Artificial
<220> FEATURE:
<223> OTHER INFORMATION: Primer

<400> SEQUENCE: 29
aaaaaaacat gttcccatac tggtccatgc tc                                     32

<210> SEQ ID NO 30
<211> LENGTH: 32
<212> TYPE: DNA
<213> ORGANISM: Artificial
<220> FEATURE:
<223> OTHER INFORMATION: Primer

<400> SEQUENCE: 30
aaaaaacata tgtgcaggtg tcgaccagaa tg                                     32

<210> SEQ ID NO 31
<211> LENGTH: 32
<212> TYPE: DNA
<213> ORGANISM: Artificial
<220> FEATURE:
<223> OTHER INFORMATION: Primer

<400> SEQUENCE: 31
aaaaaaggcg ccgcgtaacg aaataaatcc gc                                     32

<210> SEQ ID NO 32
<211> LENGTH: 20
<212> TYPE: DNA
<213> ORGANISM: Artificial
<220> FEATURE:
<223> OTHER INFORMATION: Primer

<400> SEQUENCE: 32
```
acaccaaagc ctgcatattg                                                    20

<210> SEQ ID NO 33
<211> LENGTH: 20
<212> TYPE: DNA
<213> ORGANISM: Artificial
<220> FEATURE:
<223> OTHER INFORMATION: Primer

<400> SEQUENCE: 33
cggtatcgtc gtctcagagt                                                    20

<210> SEQ ID NO 34
<211> LENGTH: 20
<212> TYPE: DNA
<213> ORGANISM: Artificial
<220> FEATURE:
<223> OTHER INFORMATION: Primer

<400> SEQUENCE: 34
cggccacaaa gaccacaaag                                                    20

<210> SEQ ID NO 35
<211> LENGTH: 20
<212> TYPE: DNA
<213> ORGANISM: Artificial
<220> FEATURE:
<223> OTHER INFORMATION: Primer

<400> SEQUENCE: 35
cggtatcgtc gtctcagagt                                                    20

<210> SEQ ID NO 36
<211> LENGTH: 20
<212> TYPE: DNA
<213> ORGANISM: Artificial
<220> FEATURE:
<223> OTHER INFORMATION: Primer

<400> SEQUENCE: 36
ggctggttgg ttgttgttgt                                                    20

<210> SEQ ID NO 37
<211> LENGTH: 20
<212> TYPE: DNA
<213> ORGANISM: Artificial
<220> FEATURE:
<223> OTHER INFORMATION: Primer

<400> SEQUENCE: 37
gtcacagcga atttcctcac                                                    20

<210> SEQ ID NO 38
<211> LENGTH: 20
<212> TYPE: DNA
<213> ORGANISM: Artificial
<220> FEATURE:
<223> OTHER INFORMATION: Primer

<400> SEQUENCE: 38
cggccacaaa gaccacaaag                                                    20

<210> SEQ ID NO 39
<211> LENGTH: 23
<212> TYPE: DNA
<213> ORGANISM: Artificial
<220> FEATURE:

<223> OTHER INFORMATION: Primer

<400> SEQUENCE: 39
aaccaaagaa ttgttgctgc ttt                                              23

<210> SEQ ID NO 40
<211> LENGTH: 25
<212> TYPE: DNA
<213> ORGANISM: Artificial
<220> FEATURE:
<223> OTHER INFORMATION: Primer

<400> SEQUENCE: 40
ttcgaaaaca cctggtggac cgttc                                            25

<210> SEQ ID NO 41
<211> LENGTH: 25
<212> TYPE: DNA
<213> ORGANISM: Artificial
<220> FEATURE:
<223> OTHER INFORMATION: Primer

<400> SEQUENCE: 41
gcggtgaccc gggagatctg aattc                                            25

<210> SEQ ID NO 42
<211> LENGTH: 12
<212> TYPE: DNA
<213> ORGANISM: Artificial
<220> FEATURE:
<223> OTHER INFORMATION: Primer

<400> SEQUENCE: 42
gaattcagat ct                                                          12

<210> SEQ ID NO 43
<211> LENGTH: 25
<212> TYPE: DNA
<213> ORGANISM: Artificial
<220> FEATURE:
<223> OTHER INFORMATION: Primer

<400> SEQUENCE: 43
gcggtgaccc gggagatctg aattc                                            25

<210> SEQ ID NO 44
<211> LENGTH: 27
<212> TYPE: DNA
<213> ORGANISM: Artificial
<220> FEATURE:
<223> OTHER INFORMATION: Primer

<400> SEQUENCE: 44
ccaattctgc agcaactggc tttaacg                                          27

<210> SEQ ID NO 45
<211> LENGTH: 25
<212> TYPE: DNA
<213> ORGANISM: Artificial
<220> FEATURE:
<223> OTHER INFORMATION: Primer

<400> SEQUENCE: 45
gcggtgaccc gggagatctg aattc                                            25

<210> SEQ ID NO 46

```
<211> LENGTH: 21
<212> TYPE: DNA
<213> ORGANISM: Artificial
<220> FEATURE:
<223> OTHER INFORMATION: Primer

<400> SEQUENCE: 46
gcctcaccat tggtctgcc c                                               21

<210> SEQ ID NO 47
<211> LENGTH: 25
<212> TYPE: DNA
<213> ORGANISM: Artificial
<220> FEATURE:
<223> OTHER INFORMATION: Primer

<400> SEQUENCE: 47
gactccccgg agtgtcgaaa tatga                                          25

<210> SEQ ID NO 48
<211> LENGTH: 24
<212> TYPE: DNA
<213> ORGANISM: Artificial
<220> FEATURE:
<223> OTHER INFORMATION: Primer

<400> SEQUENCE: 48
gtgatagcgg gtcctttcgc tacc                                           24

<210> SEQ ID NO 49
<211> LENGTH: 25
<212> TYPE: DNA
<213> ORGANISM: Artificial
<220> FEATURE:
<223> OTHER INFORMATION: Primer

<400> SEQUENCE: 49
gcggtgaccc gggagatctg aattc                                          25

<210> SEQ ID NO 50
<211> LENGTH: 12
<212> TYPE: DNA
<213> ORGANISM: Artificial
<220> FEATURE:
<223> OTHER INFORMATION: Primer

<400> SEQUENCE: 50
gaattcagat ct                                                        12

<210> SEQ ID NO 51
<211> LENGTH: 36
<212> TYPE: DNA
<213> ORGANISM: Artificial
<220> FEATURE:
<223> OTHER INFORMATION: Primer

<400> SEQUENCE: 51
gcgatctcga gatttgctgc aacggcaaca tcaatg                              36

<210> SEQ ID NO 52
<211> LENGTH: 36
<212> TYPE: DNA
<213> ORGANISM: Artificial
<220> FEATURE:
<223> OTHER INFORMATION: Primer

<400> SEQUENCE: 52
```

```
ctagcatctg attgttgttg tcgttgtttt tgtttt                         36

<210> SEQ ID NO 53
<211> LENGTH: 36
<212> TYPE: DNA
<213> ORGANISM: Artificial
<220> FEATURE:
<223> OTHER INFORMATION: Primer

<400> SEQUENCE: 53
gcgatctcga gatttgctgc aacggcaaca tcaatg                         36

<210> SEQ ID NO 54
<211> LENGTH: 36
<212> TYPE: DNA
<213> ORGANISM: Artificial
<220> FEATURE:
<223> OTHER INFORMATION: Primer

<400> SEQUENCE: 54
acttggccat ggttgttgtt gttgtcgttg tttttg                         36

<210> SEQ ID NO 55
<211> LENGTH: 44
<212> TYPE: DNA
<213> ORGANISM: Artificial
<220> FEATURE:
<223> OTHER INFORMATION: Primer

<400> SEQUENCE: 55
ccggaattcg atatctgggc wggkaatgcc aaygarttra atgc                44

<210> SEQ ID NO 56
<211> LENGTH: 44
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (33)..(33)
<223> OTHER INFORMATION: n is a, c, g, or t

<400> SEQUENCE: 56
cgcggattca ggcctcagta ngaraawgaa ccngtrttra artc                44

<210> SEQ ID NO 57
<211> LENGTH: 36
<212> TYPE: DNA
<213> ORGANISM: Artificial
<220> FEATURE:
<223> OTHER INFORMATION: Primer

<400> SEQUENCE: 57
actgtcgagc tcagtatatg gaattgacgg ctcatc                         36

<210> SEQ ID NO 58
<211> LENGTH: 38
<212> TYPE: DNA
<213> ORGANISM: Artificial
<220> FEATURE:
<223> OTHER INFORMATION: Primer

<400> SEQUENCE: 58
```

```
actgacgcgt cgacgtatca tttgtagccc acgccacc                          38
```

<210> SEQ ID NO 59
<211> LENGTH: 35
<212> TYPE: DNA
<213> ORGANISM: Artificial
<220> FEATURE:
<223> OTHER INFORMATION: Primer

<400> SEQUENCE: 59

```
cctcccccgg gctgatagaa gggtgatatg taatt                            35
```

<210> SEQ ID NO 60
<211> LENGTH: 24
<212> TYPE: DNA
<213> ORGANISM: Artificial
<220> FEATURE:
<223> OTHER INFORMATION: Primer

<400> SEQUENCE: 60

```
ccaagagtta tggggcccca gttg                                        24
```

<210> SEQ ID NO 61
<211> LENGTH: 36
<212> TYPE: DNA
<213> ORGANISM: Artificial
<220> FEATURE:
<223> OTHER INFORMATION: Primer

<400> SEQUENCE: 61

```
gcgatctcga gatttgctgc aacggcaaca tcaatg                           36
```

<210> SEQ ID NO 62
<211> LENGTH: 69
<212> TYPE: DNA
<213> ORGANISM: Artificial
<220> FEATURE:
<223> OTHER INFORMATION: Primer

<400> SEQUENCE: 62

```
tggactagta catgcatgcg gtgagaaagt agaaagcaaa cattgttgtt gttgttgtcg  60
ttgttttg                                                           69
```

<210> SEQ ID NO 63
<211> LENGTH: 42
<212> TYPE: DNA
<213> ORGANISM: Artificial
<220> FEATURE:
<223> OTHER INFORMATION: Primer

<400> SEQUENCE: 63

```
cctcccccgg ggatatcaaa gttatattat taatgattca ag                    42
```

<210> SEQ ID NO 64
<211> LENGTH: 43
<212> TYPE: DNA
<213> ORGANISM: Artificial
<220> FEATURE:
<223> OTHER INFORMATION: Primer

<400> SEQUENCE: 64

```
ggacgagagc tcgggcccat gacttcagag ttgattttga gtc                   43
```

<210> SEQ ID NO 65
<211> LENGTH: 44
<212> TYPE: DNA

```
<213> ORGANISM: Artificial
<220> FEATURE:
<223> OTHER INFORMATION: Primer

<400> SEQUENCE: 65
ggacatgcat gcgagctcaa tgcgtgacac cgccatgatg gttg          44

<210> SEQ ID NO 66
<211> LENGTH: 52
<212> TYPE: DNA
<213> ORGANISM: Artificial
<220> FEATURE:
<223> OTHER INFORMATION: Primer

<400> SEQUENCE: 66
ggacatgcat gctacgtacc ctgcagggca ccaacagcaa cacccacctg aa    52

<210> SEQ ID NO 67
<211> LENGTH: 43
<212> TYPE: DNA
<213> ORGANISM: Artificial
<220> FEATURE:
<223> OTHER INFORMATION: Primer

<400> SEQUENCE: 67
ggacatgcat gcgagctcat agttgaacaa acactggcat ttg           43

<210> SEQ ID NO 68
<211> LENGTH: 52
<212> TYPE: DNA
<213> ORGANISM: Artificial
<220> FEATURE:
<223> OTHER INFORMATION: Primer

<400> SEQUENCE: 68
ggacatgcat gctacgtacc ctgcaggtgt gtgcaactag gtttatgtgg ag    52

<210> SEQ ID NO 69
<211> LENGTH: 53
<212> TYPE: DNA
<213> ORGANISM: Artificial
<220> FEATURE:
<223> OTHER INFORMATION: Primer

<400> SEQUENCE: 69
cctcccccgg ggatatctag ttagatagct cctcctccaa tcgaattatt agc   53

<210> SEQ ID NO 70
<211> LENGTH: 42
<212> TYPE: DNA
<213> ORGANISM: Artificial
<220> FEATURE:
<223> OTHER INFORMATION: Primer

<400> SEQUENCE: 70
ggacgagagc tcgggcccta cgtctatgta tcataaattt gg            42

<210> SEQ ID NO 71
<211> LENGTH: 31
<212> TYPE: DNA
<213> ORGANISM: Artificial
<220> FEATURE:
<223> OTHER INFORMATION: Primer

<400> SEQUENCE: 71
aaaaaggcgc cggattttga gtcaccactg g                        31
```

<210> SEQ ID NO 72
<211> LENGTH: 31
<212> TYPE: DNA
<213> ORGANISM: Artificial
<220> FEATURE:
<223> OTHER INFORMATION: Primer

<400> SEQUENCE: 72
aaaaagtcga ccagccaata cagagagaga c                           31

<210> SEQ ID NO 73
<211> LENGTH: 31
<212> TYPE: DNA
<213> ORGANISM: Artificial
<220> FEATURE:
<223> OTHER INFORMATION: Primer

<400> SEQUENCE: 73
aaaaaccatg gaatgtgctt gctcgtgtgt c                           31

<210> SEQ ID NO 74
<211> LENGTH: 31
<212> TYPE: DNA
<213> ORGANISM: Artificial
<220> FEATURE:
<223> OTHER INFORMATION: Primer

<400> SEQUENCE: 74
aaaaacccgg gtgagtcgga cttgaacaac g                           31

<210> SEQ ID NO 75
<211> LENGTH: 20
<212> TYPE: DNA
<213> ORGANISM: Artificial
<220> FEATURE:
<223> OTHER INFORMATION: Primer

<400> SEQUENCE: 75
tctccagact cttgttgctg                                        20

<210> SEQ ID NO 76
<211> LENGTH: 20
<212> TYPE: DNA
<213> ORGANISM: Artificial
<220> FEATURE:
<223> OTHER INFORMATION: Primer

<400> SEQUENCE: 76
gtgaggaaga agatgcacag                                        20

<210> SEQ ID NO 77
<211> LENGTH: 20
<212> TYPE: DNA
<213> ORGANISM: Artificial
<220> FEATURE:
<223> OTHER INFORMATION: Primer

<400> SEQUENCE: 77
gcctgttgga tattctctcc                                        20

<210> SEQ ID NO 78
<211> LENGTH: 20
<212> TYPE: DNA
<213> ORGANISM: Artificial
<220> FEATURE:
<223> OTHER INFORMATION: Primer -continued

```
<400> SEQUENCE: 78
gaggacagct aggtttatgc                                                    20

<210> SEQ ID NO 79
<211> LENGTH: 1737
<212> TYPE: DNA
<213> ORGANISM: Issatchenkia orientalis
<220> FEATURE:
<221> NAME/KEY: misc_feature
<222> LOCATION: (546)..(546)
<223> OTHER INFORMATION: n is a, c, g, or t

<400> SEQUENCE: 79
atgttactca gatcactaaa ctcttctgct cgttgtgtca acaaacaac cagaacaaag          60 gttaggtatc tcagccacgt cagtggtgca agcatggcga aacctacatt gaagaacaac       120
tcgagagaat ccaacaaatc cagaaactat ctaattgctg ctgtgacagc attggctgta       180
tcaacctcaa ttggagttgc cgtacatgtg aaggacccct tgtataacga tgctaccggc       240
agtgattctc cgagaagtat atctgttgac gagtttgtca agcataattc acaaaacgac       300
tgttggattg caatcaatgg caaggtttat gatttcactg attttattcc aaaccatcca       360
ggtggggtac ctccattagt taatcatgct ggttatgatg gtactaaact ttatgagaaa       420
ttgcatccaa aagtacaat tgagaaattc ttgccaaagg ataagtttct gggtgtgtta        480
gatggtgaag cgccaaaatt ggaagcagac tatttggttg acgatgatga acaagagcga       540
ctggantatt tgggcaactt acctcctttg tcatctattc agaatgttta tgatttcgaa       600
tacttggcca agaagatttt acctaaagat gcctgggcat attattcttg tggtgccgat       660
gatgaaatca caatgagaga aaaccattat gcttatcaaa gagtttattt cagaccaaga       720
atttgtgttg atgtcaagga agttgatact tcttatgaaa tgttaggcac taaaacctct       780
gttccttttt atgtatctgc caccgctttg gctaaattag gccatcctga tggtgaatgc       840
tcaattgcta gaggcgctgg taaggaaggt gtcgttcaaa tgatttcgac cctttcctca       900
atgtcattag atgaaattgc cgctgctaga attccaggtg caacccaatg gttccaatta       960
tacattaatg aggatagaaa tgtcgctaaa ggtctggtca acatgcaga agacttgggt      1020 atgaaggcta tctttataac tgttgatgct ccttctctag gtaacagaga aaaggataaa      1080
agattaaagt ttgttaatga caccgatgtc gatttgggtg attccgcaga tcgaaacagt      1140
ggtgcttcaa aggcactatc ttcgttcatt gatgcttctg tctcttggaa tgacgtcaaa      1200
gcggtcaagt cgtggactaa attgcctgtc ttagttaaag tgttcaaac agttgaagac      1260 gttattgaag cttacgatgc tggttgtcaa ggtgttgttt tgtcaaacca cggtggtagg      1320
caactagata ctgctcctcc tccaatcgaa ttattagctg aaactgttcc aactttgaag      1380
agattgggta aattaagacc agattttgaa attttaattg acggtggtgt caaaagaggt      1440
accgatattt tgaaagcagt cgcaatcggt ggccaagatg tcagagtttc agttggtatg      1500
ggtagacctt tcttatatgc caactcttgc tatggtgaag caggtgttag aaaattaatt      1560
caaaatctaa aggatgaatt agaaatggat atgagattgt tgggtgtcac taaaatggac      1620
cagctatctt cgaaacatgt cgatactaaa cgtttgattg gtagagatgc gatcaactat      1680
ttgtatgata atgtatacag cccaatcgaa accgttaaat caacaatga agattga          1737

<210> SEQ ID NO 80
<211> LENGTH: 577
<212> TYPE: PRT
<213> ORGANISM: Issatchenkia orientalis
```

<400> SEQUENCE: 80

```
Met Leu Leu Arg Ser Leu Asn Ser Ser Ala Arg Cys Val Lys Gln Thr
1               5                   10                  15

Thr Arg Thr Lys Val Arg Tyr Leu Ser His Val Ser Gly Ala Ser Met
            20                  25                  30

Ala Lys Pro Thr Leu Lys Asn Asn Ser Arg Glu Ser Asn Lys Ser Arg
        35                  40                  45

Asn Tyr Leu Ile Ala Ala Val Thr Ala Leu Ala Val Ser Thr Ser Ile
    50                  55                  60

Gly Val Ala Val His Val Lys Asp Pro Leu Tyr Asn Asp Ala Thr Gly
65                  70                  75                  80

Ser Asp Ser Pro Arg Ser Ile Ser Val Asp Glu Phe Val Lys His Asn
                85                  90                  95

Ser Gln Asn Asp Cys Trp Ile Ala Ile Asn Gly Lys Val Tyr Asp Phe
            100                 105                 110

Thr Asp Phe Ile Pro Asn His Pro Gly Gly Val Pro Pro Leu Val Asn
        115                 120                 125

His Ala Gly Tyr Asp Gly Thr Lys Leu Tyr Glu Lys Leu His Pro Lys
    130                 135                 140

Gly Thr Ile Glu Lys Phe Leu Pro Lys Asp Lys Phe Leu Gly Val Leu
145                 150                 155                 160

Asp Gly Glu Ala Pro Lys Leu Glu Ala Asp Tyr Leu Val Asp Asp Asp
                165                 170                 175

Glu Gln Glu Arg Leu Tyr Leu Gly Asn Leu Pro Pro Leu Ser Ser Ile
            180                 185                 190

Gln Asn Val Tyr Asp Phe Glu Tyr Leu Ala Lys Lys Ile Leu Pro Lys
        195                 200                 205

Asp Ala Trp Ala Tyr Tyr Ser Cys Gly Ala Asp Glu Ile Thr Met
210                 215                 220

Arg Glu Asn His Tyr Ala Tyr Gln Arg Val Tyr Phe Arg Pro Arg Ile
225                 230                 235                 240

Cys Val Asp Val Lys Glu Val Asp Thr Ser Tyr Glu Met Leu Gly Thr
                245                 250                 255

Lys Thr Ser Val Pro Phe Tyr Val Ser Ala Thr Ala Leu Ala Lys Leu
            260                 265                 270

Gly His Pro Asp Gly Glu Cys Ser Ile Ala Arg Gly Ala Gly Lys Glu
        275                 280                 285

Gly Val Val Gln Met Ile Ser Thr Leu Ser Ser Met Ser Leu Asp Glu
    290                 295                 300

Ile Ala Ala Ala Arg Ile Pro Gly Ala Thr Gln Trp Phe Gln Leu Tyr
305                 310                 315                 320

Ile Asn Glu Asp Arg Asn Val Ala Lys Gly Leu Val Lys His Ala Glu
                325                 330                 335

Asp Leu Gly Met Lys Ala Ile Phe Ile Thr Val Asp Ala Pro Ser Leu
            340                 345                 350

Gly Asn Arg Glu Lys Asp Lys Arg Leu Lys Phe Val Asn Asp Thr Asp
        355                 360                 365

Val Asp Leu Gly Asp Ser Ala Asp Arg Asn Ser Gly Ala Ser Lys Ala
    370                 375                 380

Leu Ser Ser Phe Ile Asp Ala Ser Val Ser Trp Asn Asp Val Lys Ala
385                 390                 395                 400

Val Lys Ser Trp Thr Lys Leu Pro Val Leu Val Lys Gly Val Gln Thr
                405                 410                 415
```

-continued

```
Val Glu Asp Val Ile Glu Ala Tyr Asp Ala Gly Cys Gln Gly Val Val
            420                 425                 430

Leu Ser Asn His Gly Gly Arg Gln Leu Asp Thr Ala Pro Pro Ile
        435                 440                 445

Glu Leu Leu Ala Glu Thr Val Pro Thr Leu Lys Arg Leu Gly Lys Leu
450                 455                 460

Arg Pro Asp Phe Glu Ile Leu Ile Asp Gly Val Lys Arg Gly Thr
465                 470                 475                 480

Asp Ile Leu Lys Ala Val Ala Ile Gly Gly Gln Asp Val Arg Val Ser
                485                 490                 495

Val Gly Met Gly Arg Pro Phe Leu Tyr Ala Asn Ser Cys Tyr Gly Glu
            500                 505                 510

Ala Gly Val Arg Lys Leu Ile Gln Asn Leu Lys Asp Glu Leu Glu Met
        515                 520                 525

Asp Met Arg Leu Leu Gly Val Thr Lys Met Asp Gln Leu Ser Ser Lys
530                 535                 540

His Val Asp Thr Lys Arg Leu Ile Gly Arg Asp Ala Ile Asn Tyr Leu
545                 550                 555                 560

Tyr Asp Asn Val Tyr Ser Pro Ile Glu Thr Val Lys Phe Asn Asn Glu
                565                 570                 575

Asp
```

<210> SEQ ID NO 81
<211> LENGTH: 1698
<212> TYPE: DNA
<213> ORGANISM: Issatchenkia orientalis
<220> FEATURE:
<221> NAME/KEY: misc_feature
<222> LOCATION: (941)..(941)
<223> OTHER INFORMATION: n is a, c, g, or t
<220> FEATURE:
<221> NAME/KEY: misc_feature
<222> LOCATION: (943)..(943)
<223> OTHER INFORMATION: n is a, c, g, or t

<400> SEQUENCE: 81

```
atgttaagat cccagttcaa aaacattttg aaaaatgtta caagaaccaa ttctctaagg      60
agaactttta cttccagcac ctcaaaggct ggaaaaaatg cttcatacaa tgccaagatt     120
atatctgcaa ccgtggcctc gattgttgca gcagctggct cttatatgtt ggtccagcct     180
tcactagcta atgatgaggc acagtctgct aatccaacta ggaagatctc tgttgacgaa     240
tttgttaaac acaaccatgc cgatgattgt tggatcactg ttaacggtaa cgtctatgac     300
ttgactgatt tcatttcaat gcatccaggt ggtactaccc cattgattca aaatgcaggt     360
cacgacgcaa ctgaaattta caacaagatt catccaaagg gtacaatcga gaacttctta     420
ccaaaggaaa agcaattggg tgttttggat ggtgaagctc taaaatcga agttgtgctt      480 gacgaaaagg agaaacacag attggagttg ttgaatcatc tccctgctct ttccagaatt     540
caaaacattt atgatttcga acatattgct tctagagttt tgagcgacca agcatggaac     600
tactattcat gtggtgccga agatgaaatc accttgaggg aaaatcatta tgcttaccaa     660
agaatctact ttaagccaaa atgttgtgtc aatgttgcag aagttgatac ctctcatgaa     720 atttttaggta caaaagcttc tgttcctttc tacgttccg cagccgcttc tgcaaagttg      780
gggcacgagg atggtgaatg ttccattgct agaggtgcag gtaaggaagg cgttattcaa     840
atgatttctt ccttctcttc caactctttg gaggaaattg cagaatccag aattcctggt     900
gcaacacaat ggtttcaatt atacgttaat gaagacaagg ntnttgtgaa gaagacttta     960
```

-continued

```
aaaagggccg aaaacttggg tatgaaggcc atctttgtca ctgtggacgc tgctagtaga    1020
ggtaatagag aaaaagacat tacaatgaga attaccgaag atacagatga gttaatagac    1080
gattcttctg ttagagctgg ttctacctct ggtgcattgc cagctttcat tgacaagagg    1140
ctgacttggg atgaagttaa ggatatcatt tcatggacca agttaccagt tttgctgaag    1200
ggtgttcaaa gaactgatga tattgagaag gcaattgata ttggttgtaa gggtgttgtc    1260
ttgtccaatc atggtggtag acaattagat acttctcctc ctccaataga agttatggct    1320
gaatctgttc caatcctaaa gcaaagggt aaactggatc caaatttcag tattttcgtt    1380
gatggtggtg ttagaagagg tacagatatt ttgaaagctt tggctattgg tggcagagac    1440
tgtaaagttg ctgttggtct gggtagacct ttcctttatg caaatactgg ttatggtgaa    1500
aagggtgtca gaaaggccgt gcaaattcta agagaagaat taaaggctga catgagaatg    1560
ttgggcgtta cctctttgaa cgagctagac gactcttaca ttgacaccag aagattacta    1620
ggtagagatg ctgttaacca catatacaac aacaactact acccaatgtc taagattcaa    1680
ttcaaaaacg aaaaataa                                                 1698
```

```
<210> SEQ ID NO 82
<211> LENGTH: 565
<212> TYPE: PRT
<213> ORGANISM: Issatchenkia orientalis
<220> FEATURE:
<221> NAME/KEY: misc_feature
<222> LOCATION: (314)..(315)
<223> OTHER INFORMATION: Xaa can be any naturally occurring amino acid

<400> SEQUENCE: 82
```

| Met | Leu | Arg | Ser | Gln | Phe | Lys | Asn | Ile | Leu | Lys | Asn | Val | Asn | Lys | Asn |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

His Ser Leu Arg Arg Thr Phe Thr Ser Ser Thr Ser Lys Ala Gly Lys
             20                  25                  30

Asn Ala Ser Tyr Asn Ala Lys Ile Ile Ser Ala Thr Val Ala Ser Ile
         35                  40                  45

Val Ala Ala Ala Gly Ser Tyr Met Leu Val Gln Pro Ser Leu Ala Asn
     50                  55                  60

Asp Glu Ala Gln Ser Ala Asn Pro Thr Arg Lys Ile Ser Val Asp Glu
 65                  70                  75                  80

Phe Val Lys His Asn His Ala Asp Asp Cys Trp Ile Thr Val Asn Gly
                 85                  90                  95

Asn Val Tyr Asp Leu Thr Asp Phe Ile Ser Met His Pro Gly Gly Thr
            100                 105                 110

Thr Pro Leu Ile Gln Asn Ala Gly His Asp Ala Thr Glu Ile Tyr Asn
        115                 120                 125

Lys Ile His Pro Lys Gly Thr Ile Glu Asn Phe Leu Pro Lys Glu Lys
    130                 135                 140

Gln Leu Gly Val Leu Asp Gly Glu Ala Pro Lys Ile Glu Val Val Leu
145                 150                 155                 160

Asp Glu Lys Glu Lys His Arg Leu Glu Leu Leu Asn His Leu Pro Ala
                165                 170                 175

Leu Ser Arg Ile Gln Asn Ile Tyr Asp Phe Glu His Ile Ala Ser Arg
            180                 185                 190

Val Leu Ser Asp Gln Ala Trp Asn Tyr Tyr Ser Cys Gly Ala Glu Asp
        195                 200                 205

Glu Ile Thr Leu Arg Glu Asn His Tyr Ala Tyr Gln Arg Ile Tyr Phe
    210                 215                 220

Lys Pro Lys Cys Cys Val Asn Val Ala Glu Val Asp Thr Ser His Glu
225                 230                 235                 240

Ile Leu Gly Thr Lys Ala Ser Val Pro Phe Tyr Val Ser Ala Ala Ala
            245                 250                 255

Ser Ala Lys Leu Gly His Glu Asp Gly Glu Cys Ser Ile Ala Arg Gly
        260                 265                 270

Ala Gly Lys Glu Gly Val Ile Gln Met Ile Ser Ser Phe Ser Ser Asn
    275                 280                 285

Ser Leu Glu Glu Ile Ala Glu Ser Arg Ile Pro Gly Ala Thr Gln Trp
290                 295                 300

Phe Gln Leu Tyr Val Asn Glu Asp Lys Xaa Xaa Val Lys Lys Thr Leu
305                 310                 315                 320

Lys Arg Ala Glu Asn Leu Gly Met Lys Ala Ile Phe Val Thr Val Asp
            325                 330                 335

Ala Ala Ser Arg Gly Asn Arg Glu Lys Asp Ile Thr Met Arg Ile Thr
        340                 345                 350

Glu Asp Thr Asp Glu Leu Ile Asp Asp Ser Ser Val Arg Ala Gly Ser
    355                 360                 365

Thr Ser Gly Ala Leu Pro Ala Phe Ile Asp Lys Arg Leu Thr Trp Asp
370                 375                 380

Glu Val Lys Asp Ile Ile Ser Trp Thr Lys Leu Pro Val Leu Leu Lys
385                 390                 395                 400

Gly Val Gln Arg Thr Asp Asp Ile Glu Lys Ala Ile Asp Ile Gly Cys
            405                 410                 415

Lys Gly Val Val Leu Ser Asn His Gly Gly Arg Gln Leu Asp Thr Ser
        420                 425                 430

Pro Pro Pro Ile Glu Val Met Ala Glu Ser Val Pro Ile Leu Lys Gln
    435                 440                 445

Lys Gly Lys Leu Asp Pro Asn Phe Ser Ile Phe Val Asp Gly Gly Val
450                 455                 460

Arg Arg Gly Thr Asp Ile Leu Lys Ala Leu Ala Ile Gly Gly Arg Asp
465                 470                 475                 480

Cys Lys Val Ala Val Gly Leu Gly Arg Pro Phe Leu Tyr Ala Asn Thr
            485                 490                 495

Gly Tyr Gly Glu Lys Gly Val Arg Lys Ala Val Gln Ile Leu Arg Glu
        500                 505                 510

Glu Leu Lys Ala Asp Met Arg Met Leu Gly Val Thr Ser Leu Asn Glu
    515                 520                 525

Leu Asp Asp Ser Tyr Ile Asp Thr Arg Arg Leu Leu Gly Arg Asp Ala
530                 535                 540

Val Asn His Ile Tyr Asn Asn Tyr Tyr Pro Met Ser Lys Ile Gln
545                 550                 555                 560

Phe Lys Asn Glu Lys
            565

<210> SEQ ID NO 83
<211> LENGTH: 1778
<212> TYPE: DNA
<213> ORGANISM: Kluyveromyces marxianus

<400> SEQUENCE: 83
atgctaccaa ggttcgtggt tagatctggt gccgcaggaa gaaacctggg cttcagtttc      60
actcgtaaat gcgaccatac tttttctaagt aagactgtgc gcaatgactt gtcgcacaga   120
ccctattcta ccggaactaa cggtaatggc agtgccaatg ccggtaaaag ccaaagcggt   180

```
ttgttgtttg gtgttttgg aggtactttg atcggtggtg ggctggttgc gtactttttg    240
gggtcgaagt tcgaccagca acagagctca tctcagcaag tcagcgattt gtccattgct    300
agactagagg atttggactc gcccaagtac tgcgacaaga agacgtttgc tactgctgtc    360
gaggagttga acaggtgtt ggataacaac ccagagaact tttcggacgc caagagcgac    420
ttagactcgc actcagacac atatttcaac tcgcaccatg ccacgccaga acagagaccc    480
gaaatcgttt tgttccccg taacacggaa gacgtttcca agttactcaa gatatgccac    540
aagtactcca ttcctgtcat tccattctcc ggtgggacct cgctcgaggg ccacttcatg    600
cccacgagac cgggctcctg cgtcgttttg gacatctcca agtacatgaa ccaattatcc    660
agttgaacaa ggaagacctc gacgtggtcg tgcaaggtgg tgttccatgg aagacttga    720
acgactactt gaacgaccac gggttgttgt tcggttgcga tcctggtcca ggtgcccaga    780
tcgctggttg tattgctaac tcttgttccg aaccaatgc gtaccgttac ggtactatga    840
aagaaaacgt cgtcaacatc accatgtgtc ttgccgacgg taccatcatc aagaccaaga    900
gaagaccaag aaaatcctct gctggttaca acttgaacgg tttgatcatc ggaagcgagg    960
gtaccttggg tattgtcacc gaggcaacaa taaagtgtca cgtgagatct aactttgaaa   1020
ccgtcgctgt tgttccgttc cccagcgtgg ccgatgctgc ctcgtgctcc tcccacttga   1080
tccaggccgg tatccagctg aatgccatgg aattgttgga cgataacatg atgaagatca   1140
tcaacaagag cggtgctact tcaagaacaa actgggtcga atcaccaacc ttattcttca   1200
agattggtgg gagaagcgaa aaggccatca agaagtggt taaagaggtc gagaagatcg   1260
cctctcaaca caacaacagc aacttcgaat ttgcatctga tgaagaaact aaattggaat   1320
tgtgggaagc tagaaaagtc gctctttggt ctacgattga tgcaggtaag aagttggatc   1380
caaacgtcaa cgtttggacc accgatgttg ccgttcctat ctccaaattc gcccaggtta   1440
tcaacgatac aaaggaggaa atgaacgctt ctggattatt gacctctctt gttggtcatg   1500
ccggtgacgg taatttccat gctttcatca tttacaatgc cgaacaacgt aagaccgcag   1560
aaaccattgt cgaaaatatg gtcaagagag ccattgacgc agaaggtacc tgtaccggtg   1620
aacacggtgt tggtattggt aagagagagt ttttggttga agagttgggc gaagatacaa   1680
ttgctgtcat gagaaaattg aaacttgcct tggatccaaa gaggatcttg aaccctgaca   1740
aggtcttcaa gattgaccct aacgatcacc aacactga                           1778
```

<210> SEQ ID NO 84
<211> LENGTH: 592
<212> TYPE: PRT
<213> ORGANISM: Kluyveromyces marxianus

<400> SEQUENCE: 84

Met Leu Pro Arg Phe Val Val Arg Ser Gly Ala Ala Gly Arg Asn Leu
1               5                   10                  15

Gly Phe Ser Phe Thr Arg Lys Cys Asp His Thr Phe Leu Ser Lys Thr
            20                  25                  30

Val Arg Asn Asp Leu Ser His Arg Pro Tyr Ser Thr Gly Thr Asn Gly
        35                  40                  45

Asn Gly Ser Ala Asn Ala Gly Lys Ser Gln Ser Gly Leu Leu Phe Gly
    50                  55                  60

Val Phe Gly Gly Thr Leu Ile Gly Gly Leu Val Ala Tyr Phe Leu
65                  70                  75                  80

Gly Ser Lys Phe Asp Gln Gln Gln Ser Ser Gln Gln Val Ser Asp
            85                  90                  95

```
Leu Ser Ile Ala Arg Leu Glu Asp Leu Asp Ser Pro Lys Tyr Cys Asp
            100                 105                 110

Lys Lys Thr Phe Ala Thr Ala Val Glu Glu Leu Lys Gln Val Leu Asp
        115                 120                 125

Asn Asn Pro Glu Asn Phe Ser Asp Ala Lys Ser Asp Leu Asp Ser His
    130                 135                 140

Ser Asp Thr Tyr Phe Asn Ser His His Ala Thr Pro Glu Gln Arg Pro
145                 150                 155                 160

Glu Ile Val Leu Phe Pro Arg Asn Thr Glu Asp Val Ser Lys Leu Leu
                165                 170                 175

Lys Ile Cys His Lys Tyr Ser Ile Pro Val Ile Pro Phe Ser Gly Gly
            180                 185                 190

Thr Ser Leu Glu Gly His Phe Met Pro Thr Arg Pro Gly Ser Cys Val
        195                 200                 205

Val Leu Asp Ile Ser Lys Tyr Met Asn Gln Ile Ile Gln Leu Asn Lys
    210                 215                 220

Glu Asp Leu Asp Val Val Gln Gly Gly Val Pro Trp Glu Asp Leu
225                 230                 235                 240

Asn Asp Tyr Leu Asn Asp His Gly Leu Leu Phe Gly Cys Asp Pro Gly
                245                 250                 255

Pro Gly Ala Gln Ile Ala Gly Cys Ile Ala Asn Ser Cys Ser Gly Thr
            260                 265                 270

Asn Ala Tyr Arg Tyr Gly Thr Met Lys Glu Asn Val Val Asn Ile Thr
        275                 280                 285

Met Cys Leu Ala Asp Gly Thr Ile Ile Lys Thr Lys Arg Arg Pro Arg
    290                 295                 300

Lys Ser Ser Ala Gly Tyr Asn Leu Asn Gly Leu Ile Ile Gly Ser Glu
305                 310                 315                 320

Gly Thr Leu Gly Ile Val Thr Glu Ala Thr Ile Lys Cys His Val Arg
                325                 330                 335

Ser Asn Phe Glu Thr Val Ala Val Val Pro Phe Pro Ser Val Ala Asp
            340                 345                 350

Ala Ala Ser Cys Ser Ser His Leu Ile Gln Ala Gly Ile Gln Leu Asn
        355                 360                 365

Ala Met Glu Leu Leu Asp Asp Asn Met Met Lys Ile Ile Asn Lys Ser
    370                 375                 380

Gly Ala Thr Ser Arg Thr Asn Trp Val Glu Ser Pro Thr Leu Phe Phe
385                 390                 395                 400

Lys Ile Gly Gly Arg Ser Glu Lys Ala Ile Lys Glu Val Val Lys Glu
                405                 410                 415

Val Glu Lys Ile Ala Ser Gln His Asn Asn Ser Asn Phe Glu Phe Ala
            420                 425                 430

Ser Asp Glu Glu Thr Lys Leu Glu Leu Trp Glu Ala Arg Lys Val Ala
        435                 440                 445

Leu Trp Ser Thr Ile Asp Ala Gly Lys Lys Leu Asp Pro Asn Val Asn
    450                 455                 460

Val Trp Thr Thr Asp Val Ala Val Pro Ile Ser Lys Phe Ala Gln Val
465                 470                 475                 480

Ile Asn Asp Thr Lys Glu Glu Met Asn Ala Ser Gly Leu Leu Thr Ser
                485                 490                 495
```

-continued

```
Leu Val Gly His Ala Gly Asp Gly Asn Phe His Ala Phe Ile Ile Tyr
            500                 505                 510

Asn Ala Glu Gln Arg Lys Thr Ala Glu Thr Ile Val Glu Asn Met Val
        515                 520                 525

Lys Arg Ala Ile Asp Ala Glu Gly Thr Cys Thr Gly Glu His Gly Val
530                 535                 540

Gly Ile Gly Lys Arg Glu Phe Leu Val Glu Glu Leu Gly Glu Asp Thr
545                 550                 555                 560

Ile Ala Val Met Arg Lys Leu Lys Leu Ala Leu Asp Pro Lys Arg Ile
                565                 570                 575

Leu Asn Pro Asp Lys Val Phe Lys Ile Asp Pro Asn Asp His Gln His
            580                 585                 590
```

<210> SEQ ID NO 85
<211> LENGTH: 22
<212> TYPE: DNA
<213> ORGANISM: Artificial
<220> FEATURE:
<223> OTHER INFORMATION: Primer

<400> SEQUENCE: 85
gcgatatcaa tggtgatacc tc                                    22

<210> SEQ ID NO 86
<211> LENGTH: 21
<212> TYPE: DNA
<213> ORGANISM: Artificial
<220> FEATURE:
<223> OTHER INFORMATION: Primer

<400> SEQUENCE: 86
gaacccaagc gtacttgaaa g                                     21

<210> SEQ ID NO 87
<211> LENGTH: 32
<212> TYPE: DNA
<213> ORGANISM: Artificial
<220> FEATURE:
<223> OTHER INFORMATION: Primer

<400> SEQUENCE: 87
attaatgagc tctatgtgag tgcgtcttca gg                         32

<210> SEQ ID NO 88
<211> LENGTH: 34
<212> TYPE: DNA
<213> ORGANISM: Artificial
<220> FEATURE:
<223> OTHER INFORMATION: Primer

<400> SEQUENCE: 88
ataatttcta gatgttgatg atgtgttgaa tttg                       34

<210> SEQ ID NO 89
<211> LENGTH: 33
<212> TYPE: DNA
<213> ORGANISM: Artificial
<220> FEATURE:
<223> OTHER INFORMATION: Primer

<400> SEQUENCE: 89
gaaggatccg tgttgaatta ggtaaggttc tag                        33

<210> SEQ ID NO 90

```
<211> LENGTH: 33
<212> TYPE: DNA
<213> ORGANISM: Artificial
<220> FEATURE:
<223> OTHER INFORMATION: Primer

<400> SEQUENCE: 90
gaaactagtc ttccagtaac catatctttc ctg                             33
```

LACTIC ACID-PRODUCING YEAST CELLS HAVING NONFUNCTIONAL L- OR D-LACTATE:FERRICYTOCHROME C OXIDOREDUCTASE CELLS

This application claims benefit of U.S. Provisional Application Nos. 60/739,458 and 60/739,824, both filed Nov. 23, 2005.

This invention was made with Government support under Cooperative Agreement DE-FC36-03GO13145 awarded by the United States Department of Energy. The Government has certain rights in this invention.

This invention relates to certain genetically modified yeast, methods to make these yeast and fermentation processes to produce lactic acid using those genetically modified yeast.

Lactic acid is manufactured through an industrial fermentation process. The fermentation is conducted using various types of bacterial species, which consume sugars (principally glucose) and convert those sugars to the desired acid. As lactic acid is produced, the fermentation medium becomes increasingly acidic. Most bacteria that produce these organic acids do not perform well in strongly acidic environments-they either do not survive under those conditions or else produce the product so slowly as to be economically unviable.

For this reason, commercial acid fermentation processes are buffered by the addition of an agent which neutralizes the acid as it formed. This maintains the broth at or near a neutral pH and allows the bacteria to grow and produce efficiently. However, this converts the acid to a salt, which subsequently must be split to obtain the product in its desired acid form.

The most common buffering agent is a calcium compound, which neutralizes the organic acid to form the corresponding calcium salt. After the calcium salt is recovered from the fermentation broth, it is split by the addition of a mineral acid, typically sulphuric acid, to regenerate the organic acid and form an insoluble calcium salt of the mineral acid. This process therefore involves direct expense for the buffering agent and mineral acid as well as costs for handling and disposing the unwanted calcium salt by-product. These costs could be reduced or eliminated if the biocatalyst could grow and produce efficiently under lower pH conditions.

Yeast species have been considered as candidates for such low pH fermentations. Many yeast species naturally ferment hexose sugars to ethanol, but few if any naturally produce desired organic acids such as lactic acid. Accordingly, efforts have been made to genetically modify various yeast species to insert one or more genes that will enable the cell to produce lactic acid. In order to divert sugar metabolism from ethanol production to lactic acid production, these cells have also been genetically modified to disrupt or delete the native pyruvate decarboxylase (PDC) gene. This work is described, for example, in WO 99/14335, WO 00/71738 A1, WO 02/42471 A2, WO 03/049525 A2, WO 03/102152 A2 and WO 03/102201A2.

There remains a desire to provide even better biocatalysts for organic acid fermentation processes. In particularly, it is desirable to improve the productivities and yields of these fermentation processes, particularly in unbuffered, low pH fermentation processes.

In one aspect, this invention is a genetically modified yeast cell having at least one functional exogenous lactate dehydrogenase (LDH) gene which yeast cell is unable to grow on D-lactate, L-lactate or both D- and L-lactate as the sole carbon source.

This invention is also a genetically modified yeast cell having (a) at least one functional exogenous lactate dehydrogenase (LDH) gene integrated into its genome and (b) a deletion or disruption of at least one native L- or D-lactate:ferricytochrome c oxidoreductase gene. In preferred embodiments at least one L-lactate:ferricytochrome c oxidoreductase gene is deleted and disrupted when, said LDH gene is an L-LDH gene, and at least one native D-lactate:ferricytochrome c oxidoreductase gene is deleted or disrupted when if the LDH gene is a D-LDH gene.

This invention is also a fermentation process in which a genetically modified yeast cell of the invention is cultured under fermentation conditions in a fermentation broth that includes a fermentable sugar to produce lactic acid or a salt thereof.

This invention is also a method for producing a genetically modified yeast cell as described above, comprising (a) disrupting or deleting a native L- or D-lactate:ferricytochrome c oxidoreductase gene in a yeast cell and (b) transforming the yeast cell having the deleted or disrupted L- or D-lactate:ferricytochrome c oxidoreductase gene with a vector containing a functional exogenous LDH gene cassette to integrate the LDH gene cassette into the genome of the yeast cell. It is preferred that the LDH gene cassette includes a functional L-LDH gene in the case of a disruption or deletion of a L-lactate:ferricytochrome c oxidoreductase gene and includes a functional D-LDH gene in the case of a disruption or deletion of a D-lactate:ferricytochrome c oxidoreductase gene.

This invention is a method for producing a genetically modified yeast cell as described above, comprising a) transforming a yeast cell having a native L-lactate:ferricytochrome c oxidoreductase gene with a construct containing an exogenous L-LDH gene cassette to produce a mutant having a functional exogenous L-LDH gene integrated into its genome and then (b) disrupting or deleting the native L-lactate:ferricytochrome c oxidoreductase gene.

This invention is a method for producing a genetically modified yeast cell as described above, comprising transforming a yeast cell having a native L-lactate:ferricytochrome c oxidoreductase gene with a construct containing (a) a native L-lactate:ferricytochrome c oxidoreductase gene 5' flanking region; (b) a native L-lactate:ferricytochrome c oxidoreductase gene 3' flanking region and (c) an exogenous L-LDH gene cassette residing on the construct downstream of the native L-lactate:ferricytochrome c oxidoreductase gene 5' flanking region and upstream of the native L-lactate:ferricytochrome c oxidoreductase gene 3' flanking region, the construct being devoid of a functional L-lactate:ferricytochrome c oxidoreductase gene cassette.

This invention is still further a method for producing a genetically modified yeast cell of the first aspect, comprising a) transforming a yeast cell having a native D-lactate:ferricytochrome c oxidoreductase gene with a construct containing an exogenous D-LDH gene cassette to produce a mutant having a functional exogenous D-LDH gene integrated into its genome and then (b) disrupting or deleting the native D-lactate:ferricytochrome c oxidoreductase gene.

This invention is in addition a method for producing a genetically modified yeast cell of the first aspect, comprising transforming a yeast cell having a native D-lactate:ferricytochrome c oxidoreductase gene with a vector containing (a) a native D-lactate:ferricytochrome c oxidoreductase gene 5' flanking region; (b) a native D-lactate:ferricytochrome c oxidoreductase gene 3' flanking region and (c) an exogenous D-LDH gene cassette residing on the construct downstream of the native D-lactate:ferricytochrome c oxidoreductase gene 5' flanking region and upstream of the native D-lactate:ferricytochrome c oxidoreductase gene 3' flanking region, the vector being devoid of a functional D-lactate:ferricytochrome c oxidoreductase gene cassette.

The genetically modified cell of the invention has been found to produce lactate at higher productivities and higher lactate titers, especially under low pH conditions, than similar cells containing the same exogenous LDH gene cassette but having a functional L-lactate:ferricytochrome c oxidoreductase gene (in the case of an L-LDH gene cassette) or D-lactate:ferricytochrome c oxidoreductase gene (in the case of a D-LDH gene cassette). The transformed cells lack the ability to grow on a medium containing lactate as its sole carbon source, and so the deletion of the L- or D-lactate:ferricytochrome c oxidoreductase gene allows the transformed cells to be identified, if desired, based on the inability of the transformants to grow on lactate as the sole carbon source. In addition, the deletion of the L-lactate:ferricytochrome c oxidoreductase gene in accordance with the invention has been found to improve the acid resistance of the transformed cell, and in particular to improve its resistance to glycolic acid. This permits successful transformants to be selected using an acidic medium such as a glycolic acid-containing medium. The ability to use acids such as glycolic acid as a selective agent makes it possible to avoid using antibiotic or other resistance gene markers when transforming the strains to delete or disrupt the L-lactate:ferricytochrome c oxidoreductase gene.

Figure 2:
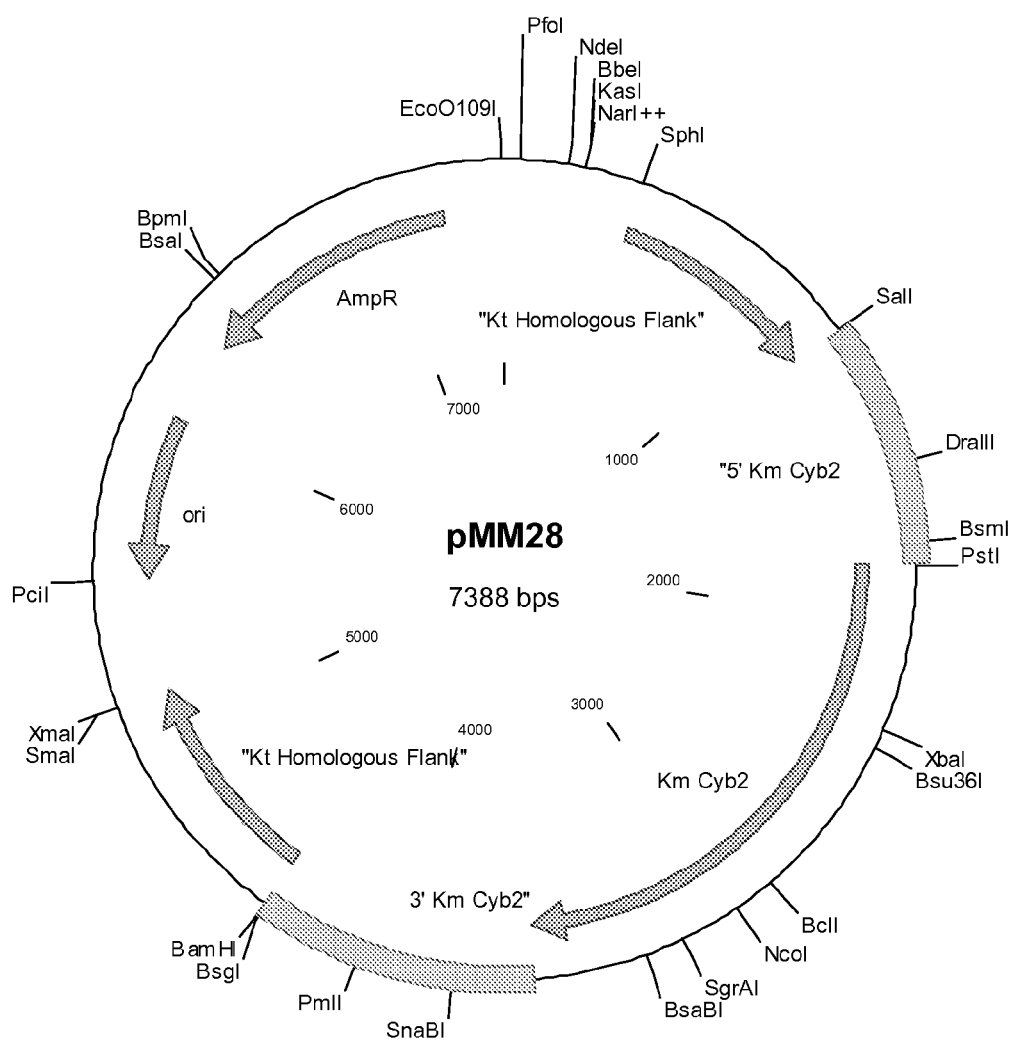
Figure 3:
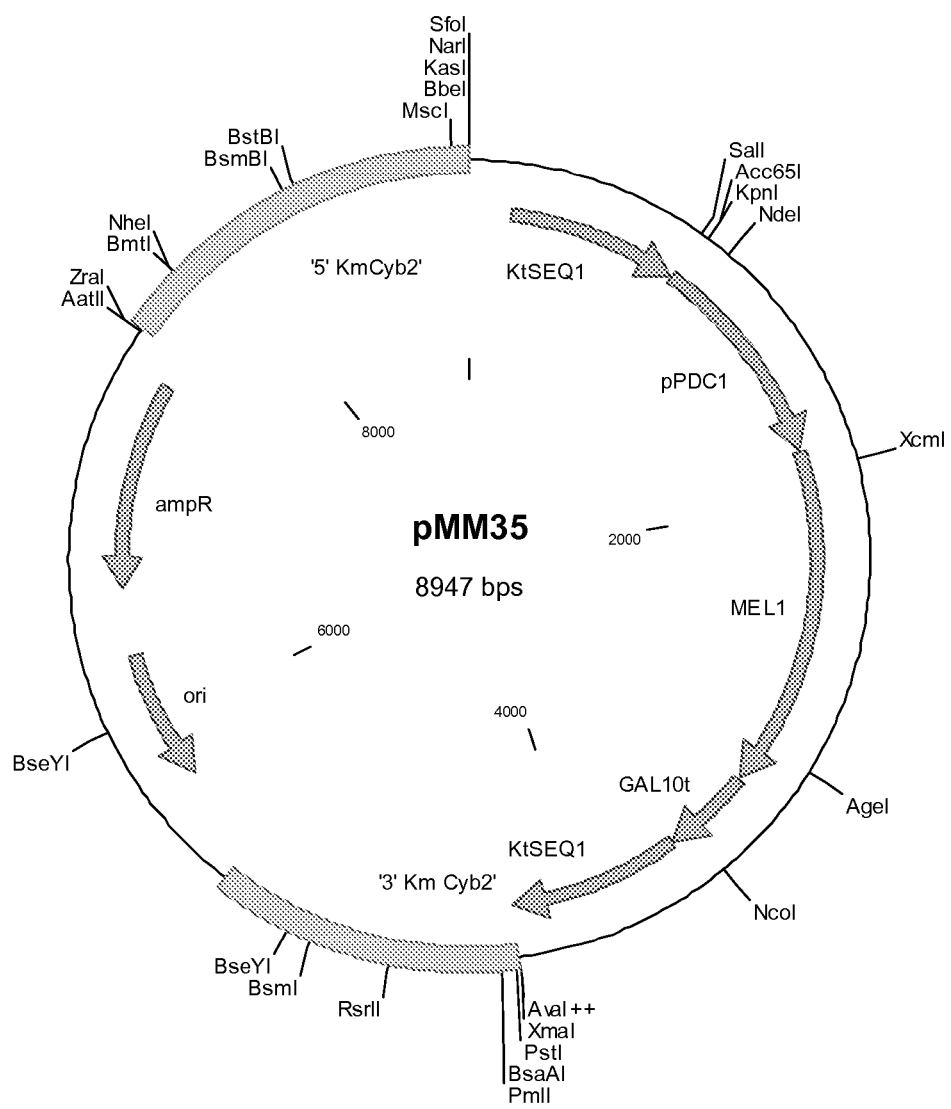
Figure 4:
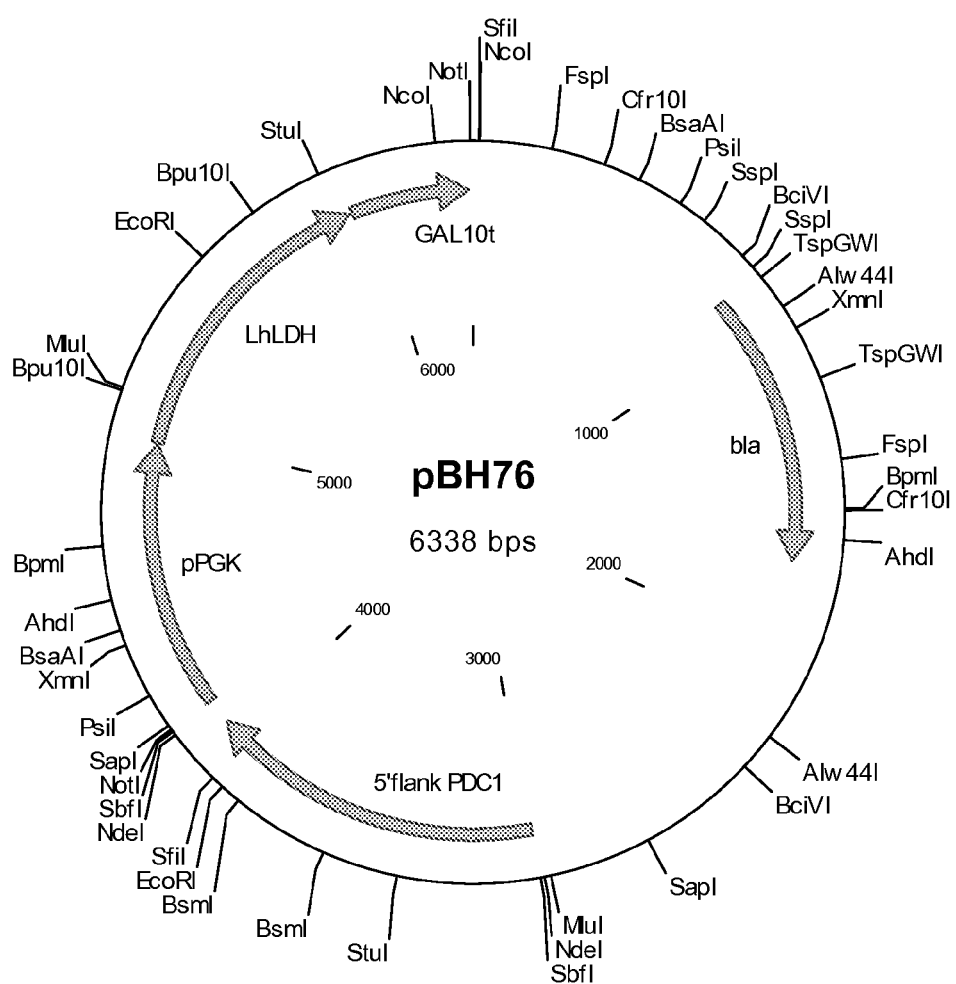
Figure 5:
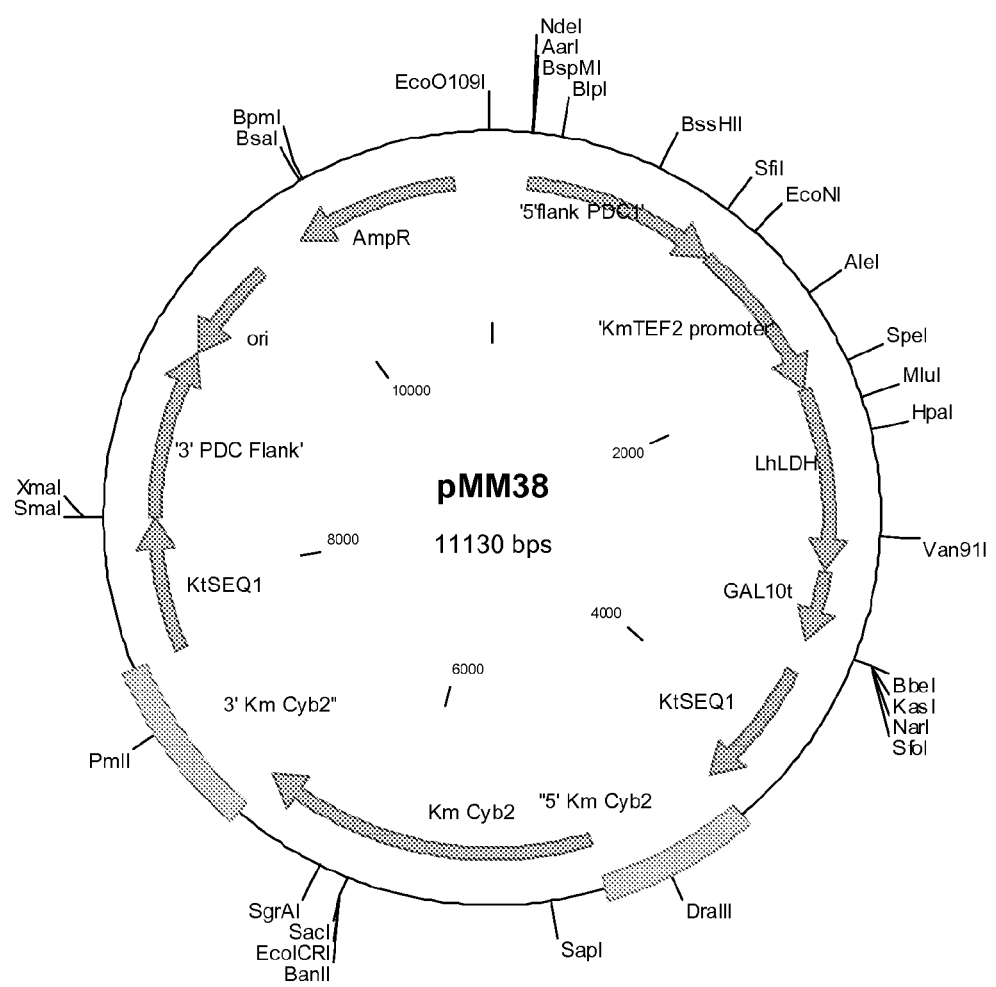
Figure 6:
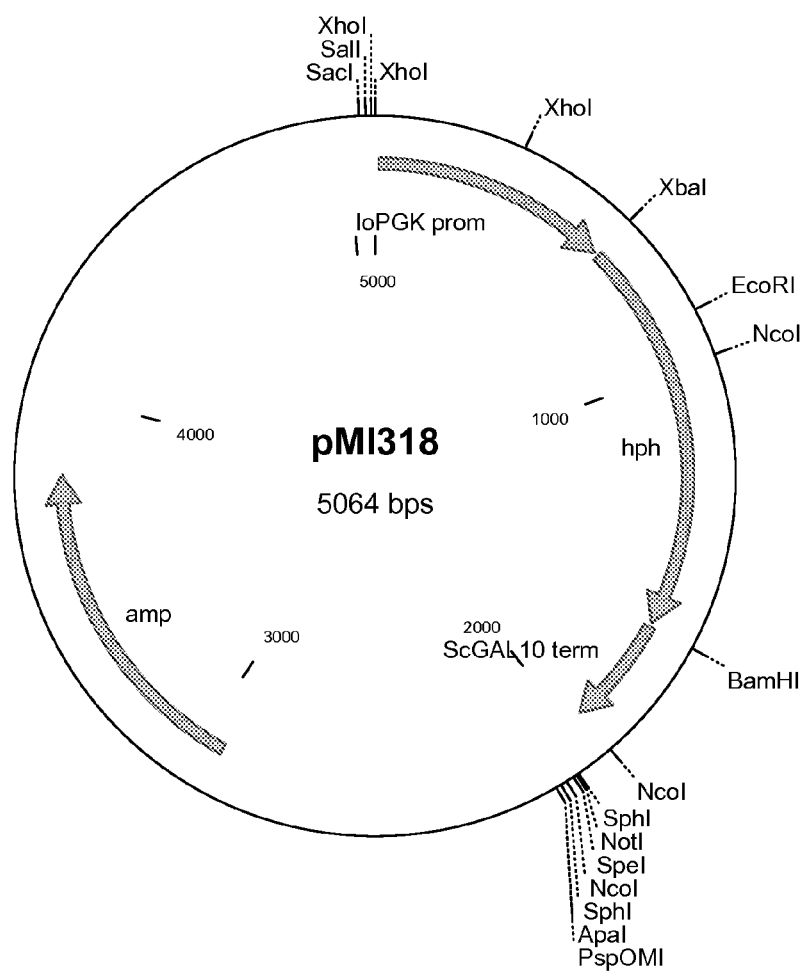
Figure 7:
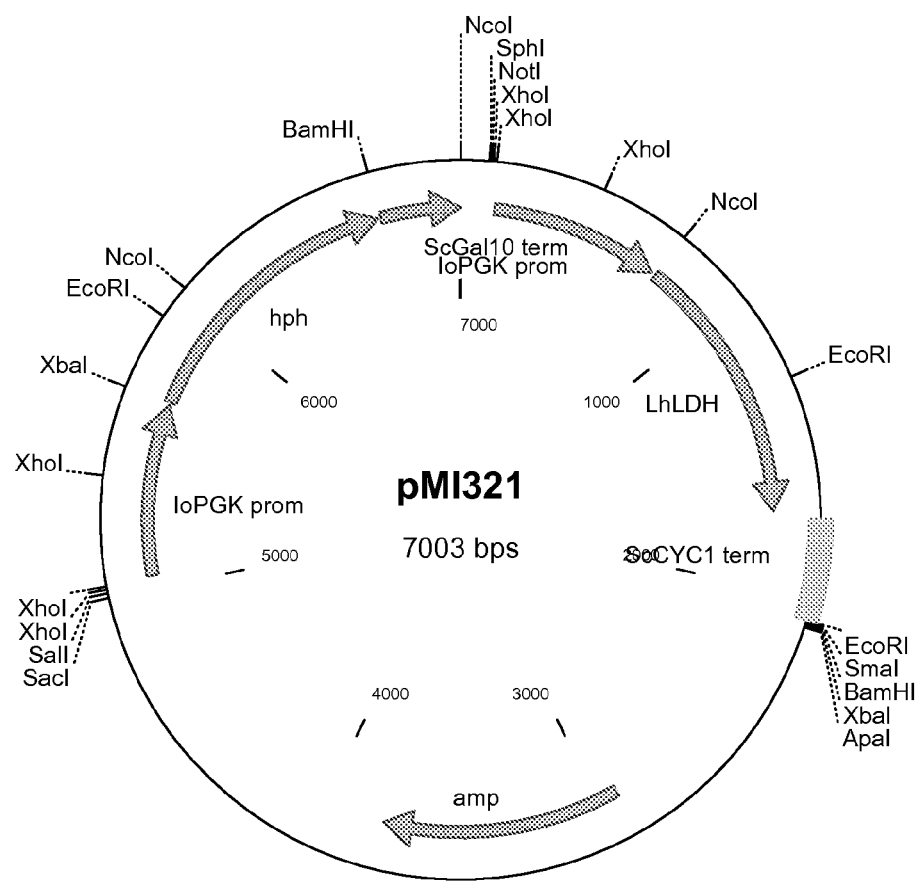
Figure 8:
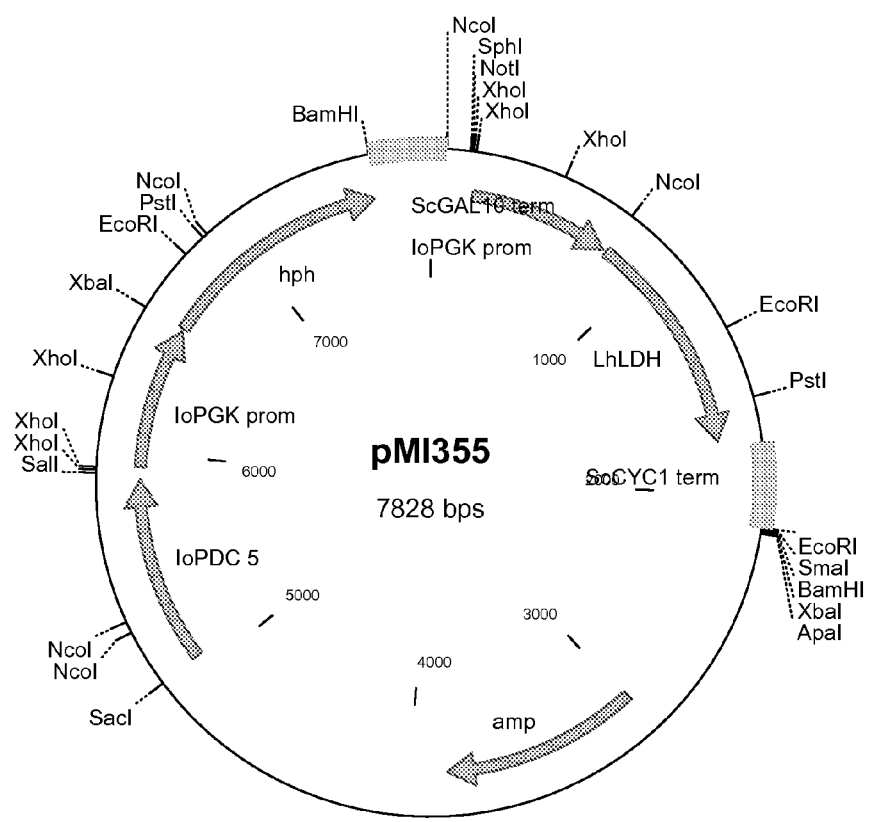
Figure 9:
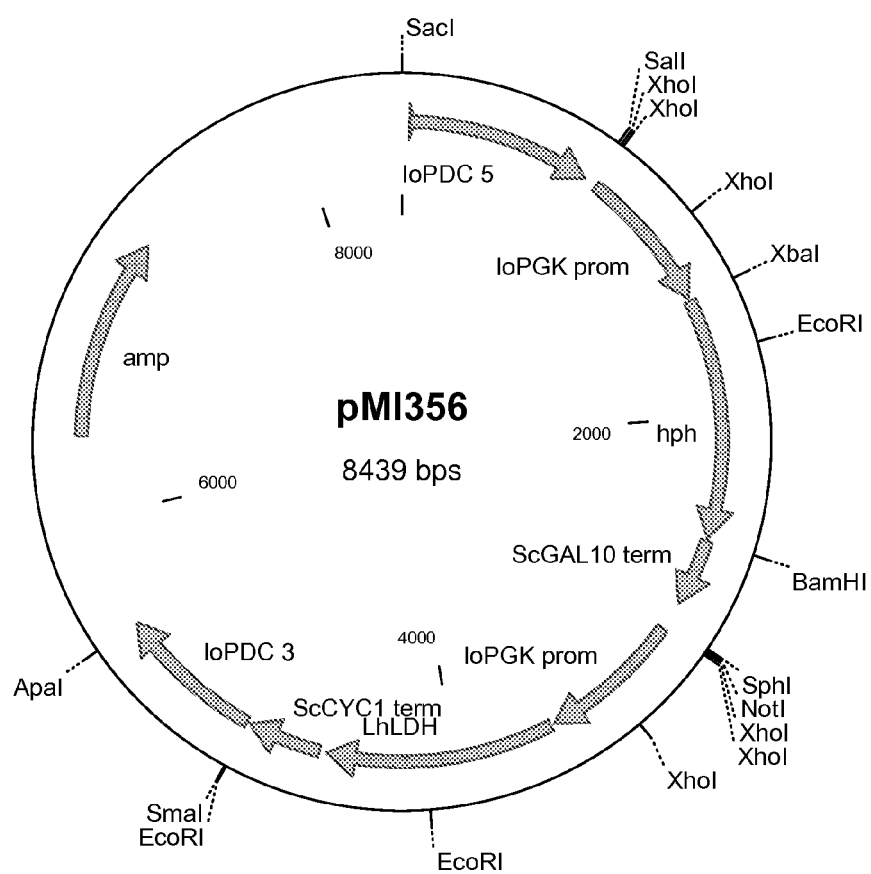
Figure 10:
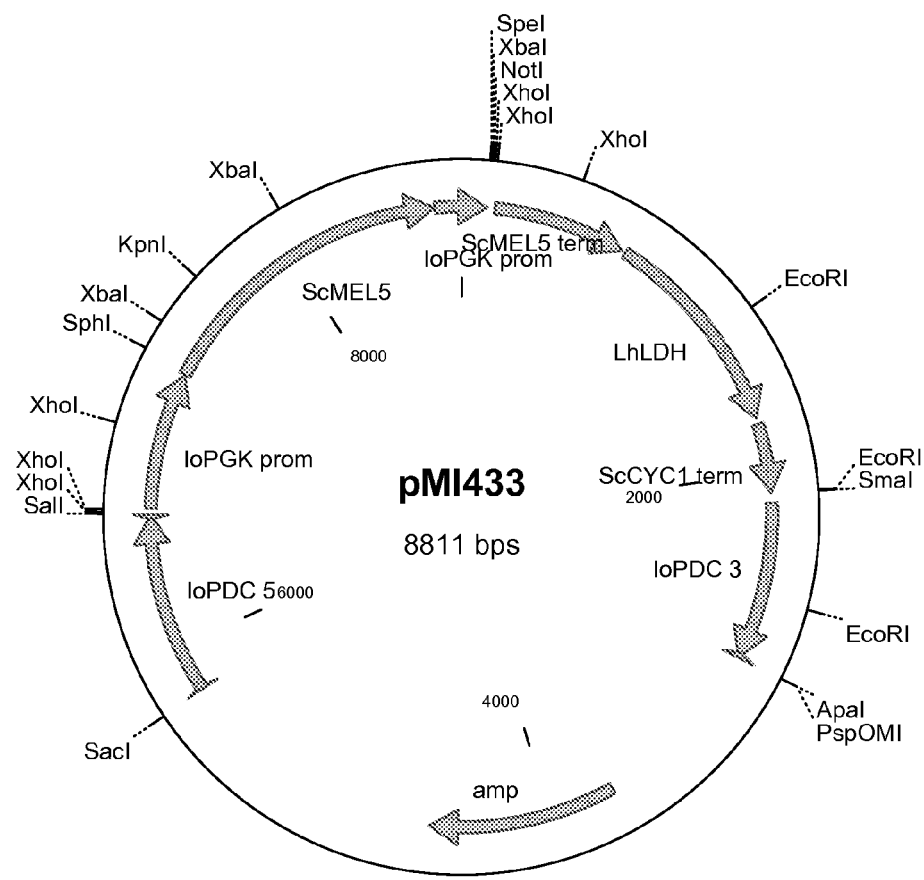
Figure 11:
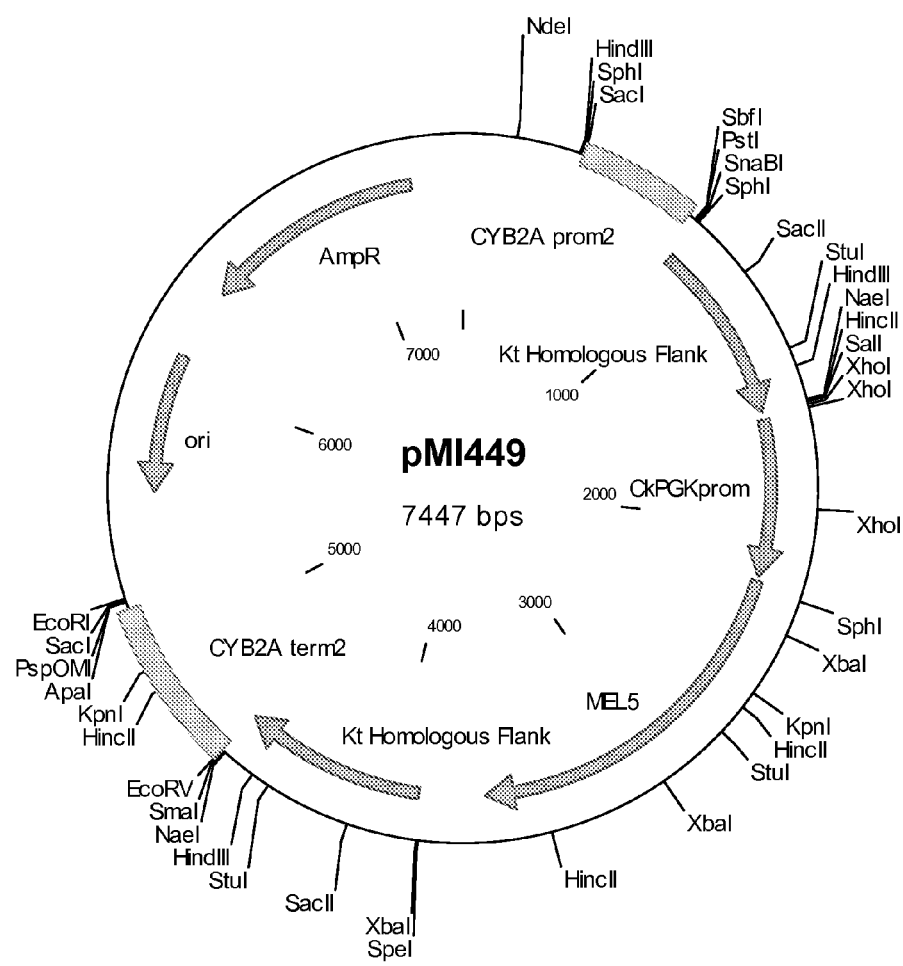
Figure 12:
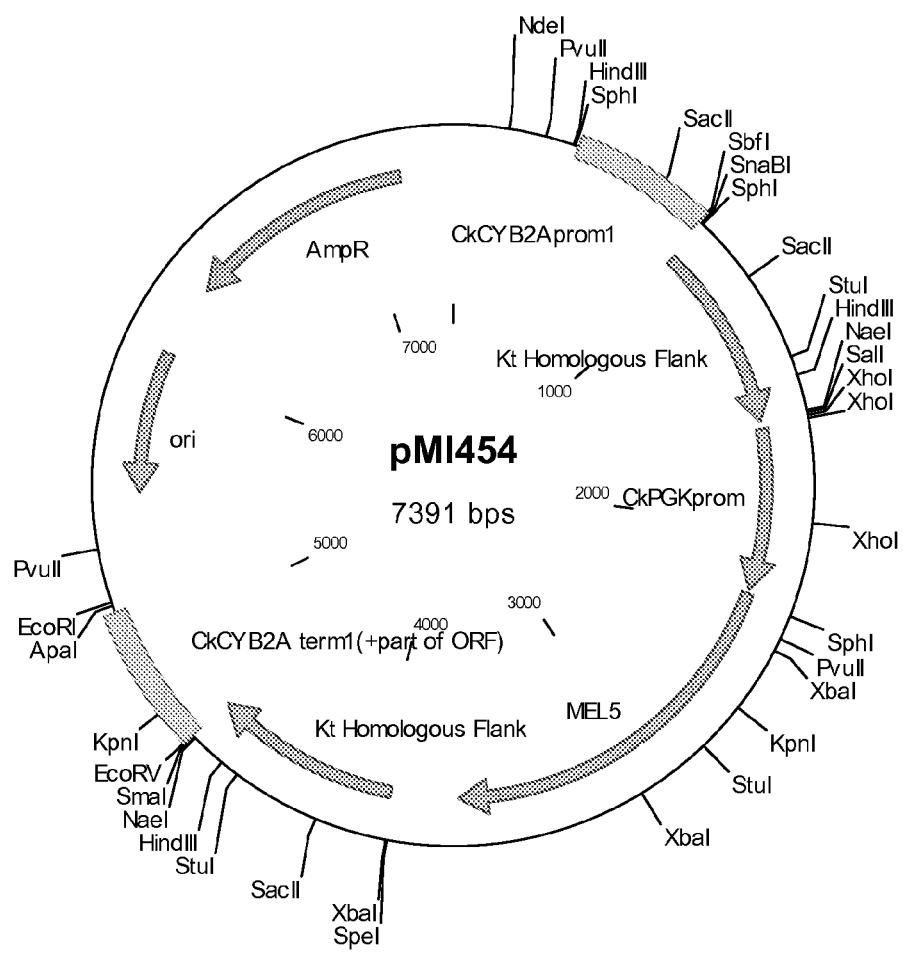
Figure 13:
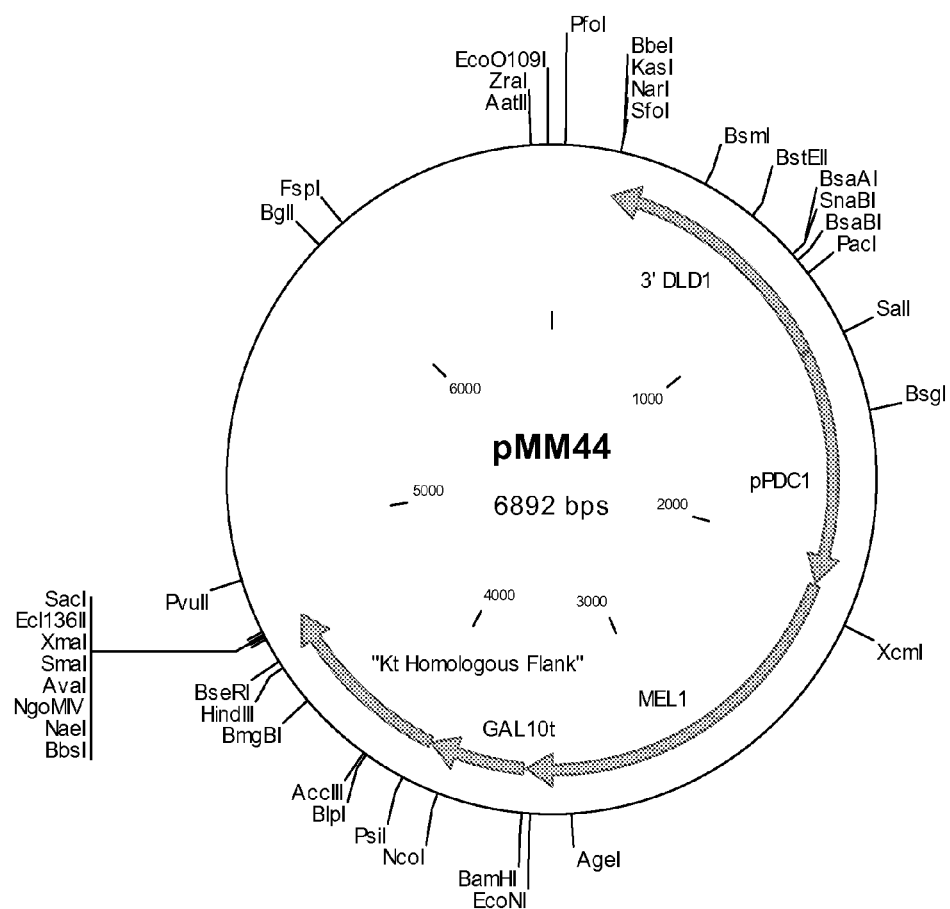
Figure 14:
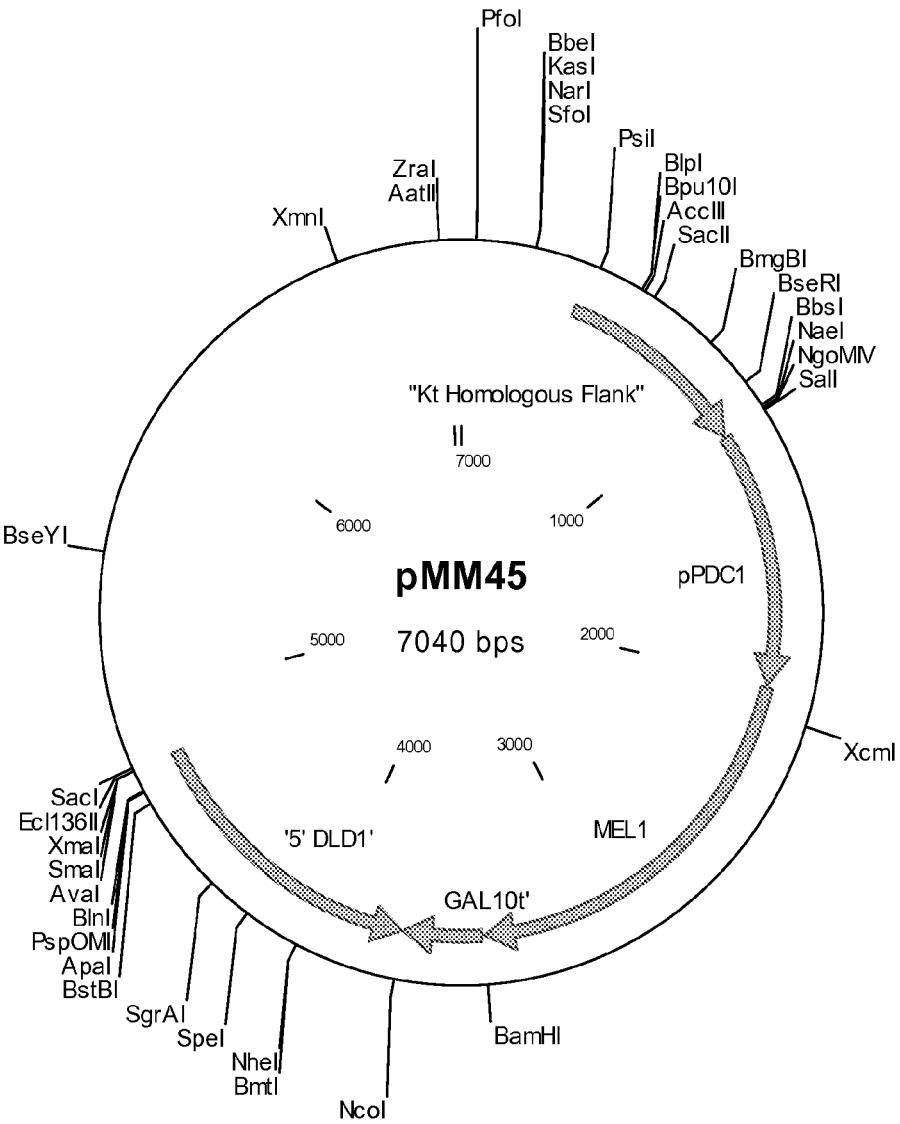
Figure 15:
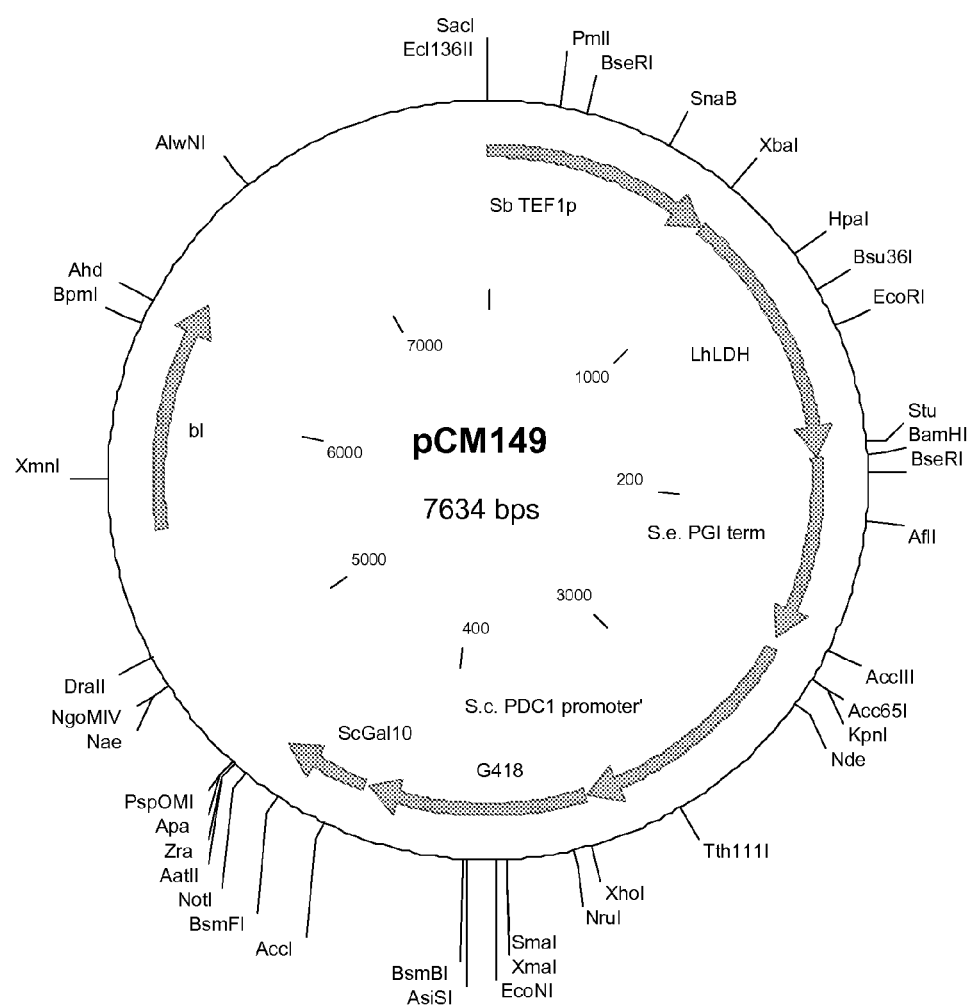

FIG. 1 is a diagram depicting the pMM22 plasmid.
FIG. 2 is a diagram depicting the pMM28 plasmid.
FIG. 3 is a diagram depicting the pMM35 plasmid.
FIG. 4 is a diagram depicting the pBH76 plasmid
FIG. 5 is a diagram depicting the pMM38 plasmid.
FIG. 6 is a diagram depicting the pMI318 plasmid.
FIG. 7 is a diagram depicting the pMI321 plasmid.
FIG. 8 is a diagram depicting the pMI355 plasmid.
FIG. 9 is a diagram depicting the pMI356 plasmid
FIG. 10 is a diagram depicting the pMI433 plasmid.
FIG. 11 is a diagram depicting the pMI449 plasmid
FIG. 12 is a diagram depicting the pMI454 plasmid.
FIG. 13 is a diagram depicting the pMM44 plasmid.
FIG. 14 is a diagram depicting the pMM45 plasmid.
FIG. 15 is a diagram depicting the pCM149 plasmid.

The genetically modified yeast of the invention is made by performing certain genetic modifications to a host yeast cell. The host yeast cell is one which as a wild-type strain, is natively capable of metabolizing at least one sugar to pyruvate. It may be natively unable to grow on lactate as a sole carbon source. *S. bulderi* is an example of such a yeast cell. In other embodiments of the invention, the cell is genetically modified to render it incapable of growing on lactate as the sole carbon source. When transformed to introduce an exogenous L-LDH gene as described herein, the host yeast cell preferably is one that as a wild-type strain has a native, functional L-lactate:ferricytochrome c oxidoreductase gene. The host yeast cell preferably is one that as a wild-type strain that contains at least one native, functional D-lactate:ferricytochrome c oxidoreductase gene if it is to be transformed with an exogenous D-LDH gene as described below.

An L-lactate:ferricytochrome c oxidoreductase is a gene that encodes for a functional L-lactate:ferricytochrome c oxidoreductase enzyme, which catalyzes the metabolisis of L-lactate to pyruvate. Although such an enzyme can help the cell metabolize the reverse reaction of pyruvate to L-lactate, it is much more efficient in catalyzing the reverse reaction of lactate back into pyruvate, so the wild-type cells produce essentially no L-lactate despite the presence of this functional gene. The L-lactate:ferricytochrome c oxidoreductase enzyme is also known by the systematic name (S)-lactate: ferricytochrome-c 2-oxidoreductase or as L-lactate dehydrogenase (cytochrome). The L-lactate:ferricyochrome c oxidoreductase gene is suitably one having a coding region identified as SEQ. ID. NO. 1 (the L-lactate:ferricyochrome c oxidoreductase gene CYB2 of a wild-type *K. marxianus* strain), SEQ. ID. NO. 79 (the CYB2A gene of a wild-type *I. orientalis* strain) or SEQ. ID. NO. 81 (the CYB2B gene of a wild-type *I. orientalis* strain), or is a gene which is at least 40%, preferably at least 75%, more preferably at least 90% and even more preferably at least 95% homologous to at least one of SEQ. ID. NOs. 1, 79 or 81. The L-lactate:ferricyochrome c oxidoreductase gene is suitably one that encodes a protein having an amino acid sequence identified as SEQ. ID. NO. 2, SEQ. ID. NO. 80 or SEQ. ID. NO. 82, or encodes for a protein which is at least 40%, preferably at least 75%, more preferably at least 90% and even more preferably at least 95% homologous to at least one of SEQ. ID. NOs. 2, 80 or 82.

A D-lactate:ferricytochrome c oxidoreductase is a gene that encodes for a functional D-lactate:ferricytochrome c oxidoreductase enzyme, which catalyzes the metabolisis of D-lactate to pyruvate much more strongly than it catalyzes the reverse reaction. The D-lactate:ferricytochrome c oxidoreductase enzyme is also known by the systematic name (R)-lactate:ferricytochrome-c 2-oxidoreductase or as D-lactate dehydrogenase (cytochrome). The D-lactate:ferricyochrome c oxidoreductase gene is suitably one having a coding region identified as SEQ. ID. NO. 83 (the D-lactate:ferricyochrome c oxidoreductase (DLD1) gene of a wild-type *K. marxianus* strain), the DLD1 gene of *S. cerevisiae*, the DLD1 gene of *I. orientalis*, or is a gene which is at least 40%, preferably at least 75%, more preferably at least 90% and even more preferably at least 95% homologous to at least one of such genes. The D-lactate:ferricyochrome c oxidoreductase gene is suitably one that encodes a protein having an amino acid sequence identified as SEQ. ID. NO. 84, a protein having the amino acid sequence of a protein encoded by the *S. cerevisiae* DLD1 gene, a protein having the amino acid sequence of a protein encoded by the *I. orientalis* DLD1 gene, or a, protein which is at least 40%, preferably at least 75%, more preferably at least 90% and even more preferably at least 95% homologous to one of those.

A "construct" is a DNA sequence that is used to transform a cell. The construct may be, for example, in the form of a circular plasmid or vector, in the form of a linearized plasmid or vector, may be a portion of a circular plasmid or vector (such as is obtained by digesting the plasmid or vector with one or more restriction enzymes), or may be a PCR product prepared using a plasmid, vector or genomic DNA as a template.

The term "native", when used herein with respect to genetic materials (e.g., a gene, promoter, terminator or other DNA sequence), refers to genetic materials that are found (apart from individual-to-individual mutations which do not affect function) within the genome of wild-type cells of that species of yeast. "Native capability" (and its variations such as "natively capable") indicates the ability of wild-type cells to perform the indicated function. For example, a cell is natively capable of metabolizing a sugar to pyruvate if wild-type cells of that species possess that capability prior to any genetic modifications. A gene is considered to be "functional" within a cell if it functions within the cell to produce an active protein.

In this invention, "exogenous" means with respect to any genetic material that the genetic material is not native to the host cell.

Suitable yeast cells include those from the genera *Candida*, *Saccharomyces*, *Shizosaccharomyes*, *Kluyveromyces*,

*Pichia, Issachenkia* and *Hansenula*. Cells from the genera *Candida, Kluyveromyces, Saccharomyces* and *Issachenkia* are particularly preferred. Especially preferred cells are *C. sonorensis, K. marxianus, K. thermotolerans, C. methanesorbosa, S. bulderi* and *I. orientalis*. Most preferred cells are *K. marxianus, S. cerevisiae, C. sonorensis* and *I. orientalis*. *I. orientalis* is referred to sometimes as *Candida krusei* or *Pichia kudriavzevii*. Suitable strains *of K. marxianus* and *C. sonorensis* include those described in WO 00/71738 A1, WO 02/42471 A2, WO 03/049525 A2, WO 03/102152 A2 and WO 03/102201A2. A suitable strain of I. orientalis is ATCC strain 32196.

The cell of the invention also contains at least one functional, exogenous lactate dehydrogenase (LDH) gene integrated into its genome. An LDH gene is one that encodes for a functional lactate dehydrogenase enzyme. LDH genes are specific to the production of either L-LDH or D-LDH, which respectively enable the cell to produce either the L- or D-lactic acid enantiomer (or their salts). It is possible that the modified cell of the invention contains both L- and D-LDH genes, and thus is capable of producing both lactic acid enantiomers. However, it is preferred that only L- or only D-LDH genes are present, so the cell produces a more optically pure lactic acid product.

Suitable LDH genes include those obtained from bacterial, fungal, yeast or mammalian sources. Examples of specific L-LDH genes are those obtained from *L. helveticus, L. casei, B. megaterium, P. acidilactici*, and bovine sources. Examples of specific D-LDH genes are those obtained from *L. helveticus, L. johnsonii, L. bulgaricus, L. delbrueckii, L. plantarum* and *L. pentosus*. Functional genes that are identical or at least 80% homologous to any of these L-LDH or D-LDH genes are suitable. The native genes obtained from any of these sources may be subjected to mutagenesis if necessary to provide a coding sequence starting with the usual eukaryotic starting codon (ATG), or for other purposes. A preferred L-LDH gene is that obtained from *L. helveticus* or one that is at least 80%, 85%, 90% or 95% homologous to such gene. Another preferred L-LDH gene is that obtained from *B. megaterium* or one that is at least 80%, 85%, 90% or 95% homologous to such gene. A preferred D-LDH gene is that obtained from *L. helveticus* or one that is at least 80%, 85%, 90% or 95% homologous to such gene.

Percent homology of DNA, RNA or other genetic material and of protein amino acid sequences can be computed conveniently using BLAST version 2.2.1 software with default parameters. Sequences having an identities score of at least XX%, using the BLAST version 2.2.1 algorithm with default parameters, are considered at least XX% homologous.

Particularly suitable LDH genes include those that encode for an enzyme with an amino acid sequence that has an identities score of at least 60%, especially at least 80%, 85% or 95%, compared with SEQ. ID. NO. 45 of WO 03/049525 or compared with SEQ. ID. NO. 49 of WO 03/049525. Particularly suitable LDH genes also include those that encode an enzyme having a protein sequence that is at least 60%, 80%, 85% or 95% homologous to SEQ ID. NO. 46 or 50 of WO 03/049525.

The transformed cell may contain a single LDH gene or multiple LDH genes, such as from 1-10 LDH genes, especially from 1-5 LDH genes. When the transformed cell contains multiple LDH genes, the individual genes may be copies of the same gene, or include copies of two or more different LDH genes. Multiple copies of the exogenous LDH gene may be integrated at a single locus (so they are adjacent each other), or at several loci within the host cell's genome.

The exogenous LDH gene is under the transcriptional control of one or more promoters and one or more terminators, both of which are functional in the modified yeast cell. As used herein, the term "promoter" refers to an untranscribed sequence located upstream (i.e., 5') to the translation start codon of a structural gene (generally within about 1 to 1000 bp, preferably 1-500 bp, especially 1-100 bp) and which controls the start of transcription of the structural gene. Similarly, the term "terminator" refers to an untranscribed sequence located downstream (i.e., 3') to the translation finish codon of a structural gene (generally within about 1 to 1000 bp, more typically 1-500 base pairs and especially 1-100 base pairs) and which controls the end of transcription of the structural gene. A promoter or terminator is "operatively linked" to a structural gene if its position in the genome relative to that of the structural gene is such that the promoter or terminator, as the case may be, performs its transcriptional control function.

Promoter and terminator sequences may be native or exogenous to the host cell.

One suitable type of promoter is at least 50%, 70%, 90%, 95% or 99% homologous to a promoter that is native to a yeast gene. A more suitable type of promoter is at least 50%, 70%, 90%, 95% or 99% homologous to a promoter for a gene that is native to the host cell. Particularly useful promoters include promoters for yeast pyruvate decarboxylase (PDC1), phosphoglycerate kinase (PGK), xylose reductase (XR), xylitol dehydrogenase (XDH), L-(+)-lactate-cytochrome c oxidoreductase (CYB2) and transcription elongation factor-1 (TEF1) and transcription elongation factor-2 (TEF2) genes, especially from the respective genes of the host cell. An especially useful promoter includes the functional portion of a promoter for a PDC1, PGK, TEF1 or TEF2 gene of the host cell or at least 80%, 85%, 90% or 95% homologous to such a promoter.

One suitable type of terminator is at least 50%, 70%, 90%, 95% or 99% homologous to a terminator for a gene that is native to a yeast cell. The terminator may be at least 90%, 95% or 99% homologous to a terminator for a gene that is native to the host cell. Particularly useful terminators include terminators for yeast pyruvate decarboxylase (PDC1), xylose reductase, (XR), xylitol dehydrogenase (XDH), L-lactate:ferricytochrome c oxidoreductase gene or iso-2-cytochrome c (CYC) genes, or a terminator from the galactose family of genes in yeast, particularly the so-called GAL10 terminator. An especially preferred terminator includes a functional portion of a terminator for a PDC1 gene of the host cell or is at least 80%, 85%, 90% or 95% homologous thereto.

The use of native (to the host cell) promoters and terminators, together with respective upstream and downstream flanking regions, can permit the targeted integration of the LDH gene into specific loci of the host cell's genome, and for simultaneous integration the LDH gene and deletion or disruption of another native gene, such as, for example, a PDC1 gene.

When multiple exogenous LDH genes are introduced into the host cell, it is possible for the different LDH genes to be under the control of different types of promoters and/or terminators.

The exogenous LDH gene may be integrated randomly into the host cell's genome or inserted at one or more targeted locations. Examples of targeted locations include the locus of one or more genes that are desirably deleted or disrupted, such as that of a PDC1 gene or that of the L- or D-lactate:ferricytochrome c oxidoreductase gene.

In embodiments in which the cell contains a functional L-LDH gene cassette, the modified cell of the invention most preferably includes a deletion or disruption of at least one native L-lactate:ferricytochrome c oxidoreductase gene. By "delete or disrupt", it is meant that the entire coding region of the gene is eliminated (deletion), or the gene, its promoter and/or its terminator region is modified (such as by deletion, insertion, or mutation) so that the gene either no longer produces the protein or an active version of the protein, or produces an enzyme with severely reduced (at least 75% reduced, preferably at least 90% reduced) activity. The deletion or disruption can be accomplished by genetic engineering methods, forced evolution or mutagenesis, followed by appropriate selection or screening to identify the desired mutants. If the cell contains multiple L-lactate:ferricytochrome c oxidoreductase genes (either multiple copies of the same gene or two or more different L-lactate:ferricytochrome c oxidoreductase paralogs), at least one of those genes is deleted or disrupted, and it is preferred to delete or disrupt all of those L-lactate:ferricytochrome c oxidoreductase genes.

In embodiments where the cell contains a functional D-LDH gene cassette, the modified cell of the invention preferably includes a deletion or disruption of at least one native D-lactate:ferricytochrome c oxidoreductase gene. As before, it is preferred to delete or disrupt all of those genes when multiple copies or alleles of the gene are present in the wild-type strain.

The genetically modified yeast cell of the invention may include additional genetic modifications that provide one or more desired attributes to the cells. An additional modification of particular interest includes a deletion or disruption of pyruvate decarboxylate gene(s), thereby reducing the cell's ability to produce ethanol.

Another additional modification of particular interest is one (or more) which individually or collectively confers to the cell the ability to ferment pentose sugars to desirable fermentation products. Among the latter type of modifications are (1) insertion of a functional xylose isomerase gene, (2) a deletion or disruption of a native gene that produces an enzyme that catalyzes the conversion of xylose to xylitol, (3) a deletion or disruption of a functional xylitol dehydrogenase gene and/or (4) modifications that cause the cell to overexpress a functional xylulokinase. Methods for introducing those modifications into yeast cells are described, for example, in WO 04/099381, incorporated herein by reference.

A third modification of particular interest is the integration of one or more functional selection marker cassettes into the host cell genome, to allow for selection of successful transformants.

Deletion or disruption of the L- or D-lactate:ferricytochrome c oxidoreductase gene can be accomplished in a variety of ways, including by genetic engineering methods, forced evolution or mutagenesis, coupled with selection or screening to identify the desired mutants.

Ultraviolet and EMS mutagenesis methods can be used to delete or disrupt the L- or D-lactate:ferricytochrome c oxidoreductase gene. These methods are well known. In these methods, cells are exposed to ultraviolet radiation or a mutagenic substance, under conditions sufficient to achieve a high kill rate (60-99%, preferably 90-99%) of the cells. Surviving cells are then plated and selected or screened for cells having deleted or disrupted L- or D-lactate:ferricytochrome c oxidoreductase genes. In the case of a deletion or disruption of an L-lactate:ferricytochrome c oxidoreductase gene, this is conveniently done by selecting for cells that are resistant to glycolic acid.

Genetic engineering of the host cell (to delete or disrupt the L- or D-lactate:ferricytochrome c oxidoreductase gene or make other modifications) is conveniently accomplished in one or more steps via the design and construction of appropriate constructs and transformation of the host cell with those constructs. Electroporation and/or chemical (such as calcium chloride- or lithium acetate-based) transformation methods can be used. The constructs in each case can either be cut with particular restriction enzymes, used as circular DNA or used as the template to generate a PCR product.

In a suitable genetic engineering method for deleting or disruption the L- or D-lactate:ferricytochrome c oxidoreductase gene, a deletion construct is conveniently assembled by first cloning two non-contiguous DNA sequences of the native L- or D-lactate:ferricytochrome c oxidoreductase gene and/or its upstream or downstream flanking regions. In this context, "non-contiguous" means that the DNA sequences are not immediately adjacent each other in the wild-type genome, but instead are separated from each other in the wild-type genome by some other genetic material (which may be as little as a single base pair). Between them, these non-contiguous sequences must include at least a portion of the coding region of the gene and/or its promoter and terminator regions. It is preferred that one of the sequences includes a 5' flanking region of the L- or D-lactate:ferricytochrome c oxidoreductase gene (including all or a portion of the promoter region and all or a portion of L- or D-lactate:ferricytochrome c oxidoreductase coding sequence), and that the other of the sequences includes a 3' flanking region of the L- or D-lactate:ferricytochrome c oxidoreductase gene (including all or a portion of the terminator region and/or all or a portion of the L- or D-lactate:ferricytochrome c oxidoreductase coding sequence). The non-contiguous sequences may be separately cloned. Alternatively, the entire region, including the 5' and 3' flanks and the L- or D-lactate:ferricytochrome c oxidoreductase gene can be cloned with subsequent deletion of at least part of the gene to render it non-functional. The non-contiguous sequences may include all or a portion of the L- or D-lactate:ferricytochrome c oxidoreductase promoter and terminator regions, respectively. A deletion construct is then produced containing the two non-contiguous sequences oriented in the same direction, and the construct is used to transform the host cell. The construct inserts at the locus of the L- or D-lactate:ferricytochrome c oxidoreductase gene in some of the transformants. A homologous double cross-over recombination event results in a deletion of the functional L- or D-lactate:ferricytochrome c oxidoreductase gene in some of the transformants Successful transformants can be (1) selected for by resistance to glycolic acid (in the case of an L-lactate:ferricytochrome c oxidoreductase gene disruption or deletion) or (2) screened for lack of ability to grow on lactate as the sole carbon source or on the basis of characteristics imparted to the cell through the use of a selection marker as described more fully below. Alternatively, screening can be performed by PCR. PCR or Southern analysis can be used to confirm that the desired deletion has taken place.

The L- or D-lactate:ferricytochrome c oxidoreductase deletion construct may also include one or more functional structural genes, notably an LDH gene cassette, inserted downstream of the 5' flanking portions of the L- or D-lactate:ferricytochrome c oxidoreductase gene and upstream of the 3' flanking portion of the L- or D-lactate:ferricytochrome c oxidoreductase gene. This approach allows for insertion of the structural gene at the locus of the L- or D-lactate:ferricytochrome c oxidoreductase gene. In a preferred case, the structural gene is an LDH gene cassette, in which case deletion of the L- or D-lactate:ferricytochrome c oxidoreductase gene and insertion of the LDH gene cassette at the locus of the L- or D-lactate:ferricytochrome c oxidoreductase gene can be accomplished in a single transformation step. Successful transformants can be identified by PCR or Southern hybridization methods, or by detecting the activity of the inserted structural gene using any convenient assay methods. In the case where the structural gene is an LDH gene, successful transformants can be identified by their ability to produce lactic acid. Transformants in which an L-lactate:ferricytochrome c oxidoreductase gene is deleted or disrupted can be selected for on the basis of their resistance to glycolic acid.

The L- or D-lactate:ferricytochrome c oxidoreductase deletion construct may also include a selection marker gene instead of or in addition to the structural gene. The use of a selection marker gene has the advantage of introducing an additional means of selecting for successful transformants, but is not required. A "selection marker gene" is one that encodes a protein needed for the survival and/or growth of the transformed cell in a selective culture medium. Typical selection marker genes encode proteins that (a) confer resistance to antibiotics or other toxins, (such as zeocin (*Streptoalloteichus hindustanus* ble bleomycin resistance gene), G418 (kanamycin-resistance gene of Tn903) or hygromycin (aminoglycoside antibiotic resistance gene from *E. coli*)), (b) complement auxotrophic deficiencies of the cell (such as amino acid leucine deficiency (*K. marxianus* LEU2 gene) or uracil deficiency (e.g., *K. marxianus* or *S. cerevisiae* URA3 gene)), (c) enables the cell to synthesize critical nutrients not available in simple media or (d) confers ability for the cell to grow on a particular carbon source, (such as the MEL1 or MEL5 genes from *S. cerevisiae*, which confers the ability to grow on melibiose as the sole carbon source. Preferred selection markers include the zeocin resistance gene, G418 resistance gene, a MEL1 and MEL5 genes and hygromycin (hph) resistance gene.

The selection marker cassette will further include promoter and terminator sequences, operatively linked to the selection marker gene, and which are operable in the host cell. Suitable promoters include those described above with respect to the LDH gene, as well as others such as are described in WO 99/14335, WO 00/71738, WO 02/42471, WO 03/102201, WO 03/102152 and WO 03/049525. An especially preferred promoter is a TEF1, PGK or PDC1 promoter (or functional portion thereof) of a yeast species, especially the host strain, or a sequence that is at least 80, 85, 90 or 95% homologous to such a TEF1, PGK or PDC1 promoter. Suitable terminators include those described above with respect to LDH genes.

The selection marker gene is similarly positioned on the construct downstream of the 5' flanking portion of the L- or D-lactate:ferricytochrome c oxidoreductase gene and upstream of the 3' flanking portion of the L- or D-lactate:ferricytochrome c oxidoreductase gene. In a portion of the cells transformed with this construct, a homologous recombination event causes the selection marker cassette (and structural gene cassette, if present) to become integrated at the CYB2 or DLD1 gene locus, respectively. Successful transformants can be selected on the basis of the characteristics imparted to it by the selection marker gene. Transformants in which the L-lactate:ferricytochrome c oxidoreductase gene becomes deleted or disrupted can be selected for based on their resistance to glycolic acid and/or screened for their inability to grow on lactate as a sole carbon source. PCR and Southern analysis methods can be used as before to characterize the transform ants.

Methods for transforming yeast strains to insert an exogenous LDH gene are described in WO 99/14335, WO 00/71738, WO 02/42471, WO 03/102201, WO 03/102152 and WO 03/049525; these methods are generally applicable for transforming cells in accordance with this invention. The constructs can either be cut with particular restriction enzymes, used as circular DNA, or used as the template to generate a PCR product.

Constructs for targeted insertion of the LDH gene cassette at the locus of the host cell's L- or D-lactate:ferricytochrome c oxidoreductase gene (with simultaneous deletion of the L- or D-lactate:ferricytochrome c oxidoreductase gene) are described above. When it is not desired to insert the LDH gene cassette at the locus of the L- or D-lactate:ferricytochrome c oxidoreductase gene, differently designed vectors are used.

Generally, an exogenous LDH gene is inserted by preparing a construct that contains the LDH gene cassette (i.e. the structural gene and associated promoter and terminator sequences). The construct may contain restriction sites of various types for linearization or fragmentation. The construct may further contain a backbone portion (such as for propagation in *E. coli*) many of which are conveniently obtained from commercially available yeast or bacterial vectors.

The LDH insertion construct preferably contains one or more selection marker gene cassettes. Targeted integration of the LDH gene cassette can be accomplished by creating a construct having non-contiguous sequences that are homologous to the upstream (5'-) and downstream (3'-) flanks of a target gene. These non-contiguous regions each are suitably from about 50 to 3000 bp in length, especially from about 200-2000 bp in length. Either or both of these non-contiguous sequences may include a portion of the coding region of the target gene as well as a portion or all of the respective promoter or terminator regions. The LDH gene cassette is arranged on the construct between the two non-contiguous sequences. A preferred target gene (other than the L- or D-lactate:ferricytochrome c oxidoreductase gene gene) is a pyruvate decarboxylate (PDC) gene, as the cell of the invention preferably has a disruption or deletion of at least one native PDC gene(s). Accordingly, preferred non-contiguous sequences are taken from the locus of a native PDC gene. However, other native genes may serve as targets for insertion of the LDH gene cassette, using non-contiguous sequences from the locus of the target gene in the LDH insertion construct in an analogous way.

The LDH cassette (including associated promoters and terminators if different from those of the target gene) and selection marker(s) (with associated promoters and terminators as may be needed) will reside on the LDH insertion construct between the regions that are homologous to the upstream and downstream flanks of the target gene, downstream from the 5' homologous flank and upstream from the 3' homologous flank.

If a selection marker cassette is used, it similarly resides on the vector between the two non-contiguous sequences taken from the locus of the target gene, as described before.

A portion of cells transformed with this construct will undergo a homologous recombination event in which the target gene is deleted or disrupted and the LDH cassette (and selection marker cassette, if present) is integrated at the locus of the target gene. In the preferred case in which the target gene is a PDC gene, the transformants will have a deletion or disruption of the PDC gene. Successful transformants can be selected for in known manner, using approaches as described above.

When the LDH insertion and the L- or D-lactate:ferricytochrome c oxidoreductase gene deletion or disruption are done sequentially, the steps can be conducted in either order, i.e., the L- or D-lactate:ferricytochrome c oxidoreductase gene deletion may be performed first, followed by the LDH insertion, or the LDH insertion can be performed first, followed by the L- or D-lactate:ferricytochrome c oxidoreductase gene deletion or disruption.

When an L-lactate:ferricytochrome c oxidoreductase gene is deleted first, it becomes possible to use the L-lactate:ferricytochrome c oxidoreductase gene itself as a selection marker during the LDH insertion and/or other subsequent transformations. In such a case, the LDH transformation vector includes a L-lactate:ferricytochrome c oxidoreductase gene cassette, in which the L-lactate:ferricytochrome c oxidoreductase gene is operatively linked to a promoter and terminator sequence. The L-lactate:ferricytochrome c oxidoreductase gene cassette is located on the LDH insertion vector between the non-contiguous sequences from the locus of the target gene. A portion of the transformants will contain both the LDH cassette and the L-lactate:ferricytochrome c oxidoreductase cassette at the locus of the target gene (which in this case is preferably a PDC gene or other gene that is desirably deleted or disrupted). Successful transformants can be selected for on the basis for their ability to grow on lactate as the sole carbon source, or by other methods as described above.

If one wants to use the L-lactate:ferricytochrome c oxidoreductase gene as a selection marker gene for a second time in accordance with this invention, it is necessary that the first L-lactate:ferricytochrome c oxidoreductase marker gene subsequently becomes deleted or disrupted. A convenient way of accomplishing this is to design a construct such that the L-lactate:ferricytochrome c oxidoreductase gene cassette is flanked by direct repeat sequences. Direct repeat sequences are identical DNA sequences, which may be native but preferably are not native to the host cell, and which are oriented in the same direction with respect to each other on the construct. The direct repeat sequences are advantageously about 50-1500 bp in length. It is not necessary that the direct repeat sequences encode for anything. In a small number of transformants, this construct permits a homologous recombination event to occur, resulting in a deletion of the L-lactate:ferricytochrome c oxidoreductase marker gene and one of the direct repeat sequences. It is usually necessary to grow transformants on nonselective media to allow for the spontaneous homologous recombination between the direct repeat sequences to occur. Also as before, cells in which the L-lactate:ferricytochrome c oxidoreductase gene has become deleted can be selected on the basis of their resistance to glycolic acid or screened for using their inability to grow on lactate as the sole carbon source.

It is preferred to delete or disrupt a native PDC gene in the host cell, so that the transformed cell has a reduced ability to produce ethanol. If the host cell contains multiple PDC genes, it is especially preferred to delete or disrupt all of the PDC genes, although it is possible to delete fewer than all such PDC genes. PDC deletion can be accomplished using methods analogous to those described in WO 99/14335, WO 02/42471, WO 03/049525, WO 03/102152 and WO 03/102201. PDC deletion can also be accomplished with simultaneous insertion of an LDH gene cassette or other structural or selection marker gene cassette. In a method of particular interest, (1) sequences from the locus of the PDC gene(s) are cloned, optionally together with a portion of the functional PDC gene; (2) a construct containing the non-contiguous sequences is produced (optionally containing a non-functional portion of the PDC structural gene), and (3) the host cell is transformed with the construct. A homologous recombination event results in a deletion or disruption of the functional PDC gene in a portion of the transformants. This can be repeated if necessary to delete or disrupt multiple PDC genes. In some yeast species, such as *I. orientalis*, multiple PDC genes or alleles exist that are closely homologous. It has been found that in such instances non-contiguous sequences taken from the locus of either gene can be used in the construct to delete or disrupt both of the PDC genes. The construct used to disrupt the PDC gene(s) may include one or more functional structural genes inserted downstream of the 5' flanking portion of the native PDC gene and upstream of the 3' flanking portions of the native PDC gene. The structural gene preferably is part of a cassette that includes functional promoter and terminator sequences operatively linked to the structural gene. This approach allows for the deletion of the PDC gene and insertion of the functional gene cassette in a single transformation step. The construct may include a selection marker gene cassette instead of or in addition to the structural gene. Again, the selection marker gene cassette is positioned on the vector as before, between the non-contiguous sequences taken from the locus of the PDC gene being targeted, and becomes inserted in the locus of the functional PDC gene in a portion of the transformants.

Suitable methods for inserting a functional xylose isomerase gene, deleting or disrupting a native gene that produces an enzyme that catalyzes the conversion of xylose to xylitol, deleting or disrupting a functional xylitol dehydrogenase gene modifying the cell to overexpress a functional xylulokinase are described, for example, in WO 04/099381, incorporated herein by reference.

In the fermentation process of the invention, the cell of the invention is cultivated in a fermentation medium that includes a sugar that is fermentable by the transformed cell. The sugar may be a hexose sugar such as glucose, glycan or other polymer of glucose, glucose oligomers such as maltose, maltotriose and isomaltotriose, panose, fructose, and fructose oligomers. If the cell natively has or is modified to impart an ability to ferment pentose sugars, the fermentation medium may include a pentose sugar such as xylose, xylan or other oligomer of xylose. Such pentose sugars are suitably hydrolysates of a hemicelluose-containing biomass. In case of oligomeric sugars, it may be necessary to add enzymes to the fermentation broth in order to digest these to the corresponding monomeric sugar for fermentation by the cell.

The medium will typically contain nutrients as required by the particular cell, including a source of nitrogen (such as amino acids, proteins, inorganic nitrogen sources such as ammonia or ammonium salts, and the like), and various vitamins, minerals and the like.

Other fermentation conditions, such as temperature, cell density, selection of substrate(s), selection of nutrients, and the like are not considered to be critical to the invention and are generally selected to provide an economical process. Temperatures during each of the growth phase and the production phase may range from above the freezing temperature of the medium to about 50° C., although this depends to some extent on the ability of the strain to tolerate elevated temperatures. A preferred temperature, particularly during the production phase, is from about 30-45° C.

During the production phase, the concentration of cells in the fermentation medium is typically in the range of about 0.1-20, preferably about 0.1-5, even more preferably about 1-3 g dry cells/liter of fermentation medium.

The fermentation may be conducted aerobically, microaerobically or anaerobically. If desired, oxygen uptake rate can be used as a process control, as described in WO 03/102200. The cells of the invention exhibit a good ability to ferment sugars to lactic acid or lactic acid/ethanol mixtures, at good volumetric and specific productivities under even anaerobic conditions.

The medium may be buffered during the production phase of the fermentation so that the pH is maintained in a range of about 3.5 to about 9.0, such as from about 4.5 to about 7.0. Suitable buffering agents are basic materials that neutralize lactic acid as it is formed, and include, for example, calcium hydroxide, calcium carbonate, sodium hydroxide, potassium hydroxide, potassium carbonate, sodium carbonate, ammonium carbonate, ammonia, ammonium hydroxide and the like. In general, those buffering agents that have been used in conventional fermentation processes are also suitable here.

In a buffered fermentation, acidic fermentation products such as lactic acid are neutralized as they are formed to the corresponding lactate salt. Recovery of the acid therefore involves regenerating the free acid. This is typically done by removing the cells and acidulating the fermentation broth with a strong acid such as sulfuric acid. A salt by-product is formed (gypsum in the case where a calcium salt is the neutralizing agent and sulfuric acid is the acidulating agent), which is separated from the acid. The acid is then recovered through techniques such as liquid-liquid extraction, distillation, absorption, etc., such as are described in T. B. Vickroy, Vol. 3, Chapter 38 of Comprehensive Biotechnology, (ed. M. Moo-Young), Pergamon, Oxford, 1985; R. Datta, et al., FEMS Microbiol. Rev., 1995, 16:221-231; U.S. Pat. Nos. 4,275,234, 4,771,001, 5,132,456, 5,420,304, 5,510,526, 5,641,406, and 5,831,122, and WO 93/00440.

It is preferred, however, to allow the pH of the fermentation medium to drop from a starting pH that is typically 5.5 or higher, to at or below the pKa of the acid fermentation product, such as in the range of about 1.5 to about 3.5, in the range of from about 1.5 to about 3.0, or in the range from about 1.5 to about 2.5. The cells of this invention to have an unexpected ability to grow and produce well even in non-buffered fermentation media where the final pH falls below 3.5, below 3.0, below 2.5, and even below 2.0.

It is also possible to conduct the fermentation by maintaining the pH at or below the pKa of lactic acid throughout the process. In such a case, the pH of the fermentation broth is adjusted to at or below the pKa of lactic acid prior to or at the start of the fermentation process, and maintained at that level as the fermentation proceeds. In this embodiment, the pH is preferably maintained within the range of about 1.5 to about 3.5, in the range of from about 1.5 to about 3.0, or in the range from about 1.5 to about 2.5.

Recovery of lactic acid from a low pH fermentation medium can be conducted using methods such as those described in U.S. Pat. Nos. 6,229,046.

The process of the invention can be conducted continuously, batch-wise, or some combination thereof.

The deletion or disruption of the L- or D-lactate:ferricytochrome c oxidoreductase gene, as the case may be, can lead to several benefits. Lactic acid titers are often improved. This is seen especially when the host cell is a Kluyveromyces strain, such as Kluyveromyces marxianus. Yields to lactate as well as lactate production rates are increased as well, compared to similar strains that do not have the L-lactate:ferricytochrome c oxidoreductase deletion. Again, this is especially seen in modified Kluyveromyces strains. A further advantage is that low pyruvate production is seen.

The following examples are provided to illustrate the invention, but are not intended to limit the scope thereof. All parts and percentages are by weight unless otherwise indicated.

EXAMPLE 1A

Mutagenesis of K. marxianus strain CD607 and Selection of Mutant Strain (CD635) having Resistance to Glycolic Acid K. marxianus strain CD607 is described in Example 3D of WO 03/102152. This strain has a deletion of its pyruvate decarboxylase gene and an insertion of an exogenous lactate dehydrogenase gene at that locus. Cells of strain CD607 are subjected to mutagenesis via exposure to ultraviolet light or ethyl methanesulfonate, according to the following protocols:

UV Mutagenesis

Cells from a fresh YPD (Difco #0427-17, Sparks, Md., containing 10 g/L yeast extract, 20 g/L peptone, 20 g/L dextrose and 15 g/L agar) plate are resuspended in 2 mL of yeast peptone+ and additional 50 g/L glucose to an approximate $OD_{600}$ of 6. Ten 125 µl aliquots of this cell suspension are pipeted into ten wells of a 300 µl 96-well microtiter plate. The microtiter plate is exposed to 12,500 µJoule/cm$^2$ of UV light to kill 90-99% of the cells. Two additional 125 µl aliquots of the cell suspension are then added to the microtiter plate as mock-treated controls. The cell suspensions from each of the twelve wells are transferred to 1.5 mL microfuge tubes. The twelve microfuge tubes are then incubated in darkness overnight at 30° C. with agitation (225 rpm) to allow the cells to recover prior to plating onto selection plates.

100 µl aliquots from nine of the UV-treated cell suspensions and from one of the mock-treated cell suspensions are then plated onto a potato dextrose agar (PDA, Difco Laboratories, Cat. No. 0013-17, Sparks, Md.)+15 g/L glycolic acid plate to select for glycolic acid-resistant strains. These plates are incubated at 30° C. for several days until colonies appear. A single colony is isolated from each of the nine plates for further analysis.

EMS Mutagenesis

Cells from a fresh YPD plate are resuspended in 2 mL of phosphate-buffered saline to an approximate $OD_{600}$ of 6. Twelve 200 µl aliquots of this cell suspension are pipeted into twelve 14 mL snap-cap tubes, and 4 µL of ethyl methanesulfonate (EMS, Sigma Chemical Co., St. Louis, Mo., catalog # M0880, 1.17 g/mL solution) is added to ten of the twelve tubes. The remaining two tubes serve as mock-treated controls. The tubes are then incubated at 30° C. with agitation (225 rpm) for 30 minutes, again to kill 90-99% of the cells. Following exposure to EMS, the cells from the twelve tubes are pelleted, washed twice with 5.0% $Na_2S_2O_3$ to neutralize the EMS and washed once with water. The cells are resuspended in 100 µL YPD media and incubated for 6 hours at 30° C. with agitation (225 rpm) to allow the cells to recover prior to plating onto selection plates.

Following recovery, 100 µL from nine of the EMS-treated cell suspensions and from one of the mock-treated cell suspension are plated onto a PDA+15 g/L glycolic acid plate to select for resistance to glycolic acid. These plates are incubated at 30° C. for several days until colonies appear. A single colony is isolated for further analysis.

Screening of the mutagenized cells is done as follows. Approximately 2×10$^8$ cells that have been mutagenized in one of the processes just described are plated onto (PDA) plates containing 15 g/L glycolic acid and incubated at 30° C. Colonies that grow on these plates are grown overnight in baffled shake flasks at 30° C. and 225 rpm agitation in YP (10 g/L yeast extract, 20 g/L peptone)+100 g/L glucose without buffer. Production flasks are then inoculated with 2 g/L cell dry weight from these shake flasks. The production flasks are cultured at 30° C. and 70 rpm agitation in YP+50 g/L glucose.

Samples are withdrawn periodically to measure glucose, lactate, ethanol and pyruvate by HPLC using methods such as described in Example 1M of WO 03/102201.

One strain is designated strain CD635. Strain CD635 results from the UV mutagenesis treatment described above. Strain CD635 produces about 13 g/L lactate after 88 hours, compared to less than 9 g/L for the parent strain, CD607. Strain CD635 consumes slightly more glucose than strain CD607 during that time period, and achieves a significantly higher yield to lactate. Strain CD635 is able to grow on lactate as the sole carbon source.

EXAMPLE 1B

Further Mutagenesis of *K. marxianus* Strain CD635 and Selection of Mutant Strains (CD832, CD839, CD840, CD841, CD850, CD851 and CD853) having Resistance to Glycolic Acid Cells of strain CD635 (Example 1A) are subjected to mutagenesis using the methods described in Example 1A, with the resulting mutagenized cells being selected for colonies that are able to grow on PDA containing 25 g/L glycolic acid. From a total of 23 mutagenesis events, approximately $5.9 \times 10^9$ cells are plated, from which several colonies are produced which are resistant to glycolic acid. Some of these colonies result from mutagenesis with EMS, others result from mutagenesis with UV light, and still others result from spontaneous mutations.

The glycolic acid-resistant colonies are separately grown overnight in YP+100 g/L glucose in shake flasks at 30° C. and 250 rpm agitation. Biomass is collected by centrifugation and 2 g/L dry weight of cells are inoculated into 50 mL YP+50 g/L glucose in a baffled shake flask. The flasks are cultivated at 30° C. and 250 rpm agitation for approximately 92 hours. Seven mutants that produce significantly higher final lactate titers, compared to parent strains CD607 and CD635, are designated as strains, CD832, CD839, CD840, CD841, CD850, CD851 and CD853.

Strains CD832, CD839, CD840, CD841, CD850, CD851 and CD853 are unable to grow on lactate as the sole carbon source, indicating that the Km CYB2 gene has become non-functional in these mutants. Therefore, the KmCYB2 coding region plus ~500 bp up and downstream from the KmCYB2 coding region is separately amplified for each of these strains using PCR with high fidelity FailSafe enzyme and genomic DNA as the template. The resulting ~2.75 kbp PCR products are purified via Qiagen column purification and sequenced over the entire KmCYB2 coding region.

Strain CD635 can grow on lactate as the sole carbon source, which indicates that it contains a functional KmCYB2 gene. Sequencing of the CYB2 gene from CD635 confirms that it has the wild-type CYB2 sequence. The DNA sequence of the KmCYB2 gene of strain CD635 is given as SEQ. ID. NO. 1. The amino acid sequence of the protein encoded by that CYB2 gene is given as SEQ. ID. NO. 2.

Strains CD832, CD839, CD840, CD841, CD850, CD851 and CD853 all lack the ability to grow on lactate as the sole carbon source, and have an increased resistance to glycolic acid compared with strain CD607. Each of these characteristics indicate that these strains lack a functional KmCYB2 gene. The DNA sequences within the KmCYB2 coding regions for these strains in each case show mutations within the coding portion of the KmCYB2 gene, compared with the KmCYB2 gene of strain CD635, which has the wild-type CYB2 sequence. Amino acid sequences for the enzymes produced by these coding regions also show differences. The differences in the DNA and amino acid sequences are:

Strain CD832: a point mutation at amino acid position 457 causes a nonsense mutation, changing an arginine to a stop codon. This mutation truncates the protein by 135 amino acids.

Strain CD839: a point mutation at amino acid position 272 causes a missense mutation, changing a proline to a threonine.

Strain CD840: a point mutation at amino acid position 222 causes a nonsense mutation, changing a tryptophan to a stop codon. This mutation truncates the protein by 370 amino acids.

Strain CD841: a point mutation at amino acid position 147 changes a histidine to a tyrosine.

Strain CD850: a double point mutation at amino acid position 309 changes a serine to a phenylalanine.

Strain CD851: a two-base pair deletion at base pair 219 (amino acid position 74) causes a frame-shift mutation, resulting in a stop codon at amino acid position 76 and truncating the protein.

Strain CD853: a four-base insertion at amino acid position 62 causes a frame-shift mutation, resulting in a stop codon at amino acid position 76 and truncating the protein.

EXAMPLE 2A

Construction of a Plasmid (pMM22, FIG. 1) Containing a G418 Resistance Gene Cassette between the 5' and 3' Flanking Regions of the *K. marxianus* CYB2 Gene The *K. marxianus* L-lactate:ferricytochrome c oxidoreductase gene (KmCYB2) gene coding region is identified within the genomic DNA sequence of a wild-type strain of *K. marxianus* (designated CD21, ATCC 52486) by comparing homology to the known homology of the *S. cerevisiae* L-lactate:ferricytochrome c oxidoreductase gene gene. A ~2 kbp flanking region directly 5' of the KmCYB2 coding region is amplified, with introduction of MluI and PstI restriction sites, by PCR using primers identified as SEQ. ID. NO. 3 and SEQ. ID. NO. 4 and genomic DNA as the template. Similarly, a ~2 kbp flanking region directly 3' of the CYB2 coding region is amplified with introduction of ApaI and NgoMIV restriction sites by PCR using primers identified as SEQ. ID. NO. 5 and SEQ. ID. NO. 6 and genomic DNA as the template.

A plasmid designated pVR29 (described in Example 1C and FIG. 4 of WO 03/102152) is digested with MluI and PstI and the 5' KmCYB2 flank is ligated to the resulting fragment to produce a plasmid designated as pMM21. Plasmid pMM21 contains the KmCYB2 5' flank upstream of a G418 resistance gene cassette.

Plasmid pMM21 is digested with ApaI and NgoMIV and the resulting fragment is ligated to the 3' KmCYB2 flank to produce a plasmid designated pMM22 (FIG. 1). Plasmid pMM22 contains the KmCYB2 5' flank upstream of the G418 resistance gene cassette, and the KmCYB2 3' flank downstream from the G418 resistance gene cassette.

EXAMPLE 2B

Generation of a *K. marixanus* Mutant (CD936) with an Integrated LDH Gene, Deleted PDC Gene and Deleted KmCYB2 Gene by Transforming *K. marxianus* Strain CD607 with Plasmid pMM22 (FIG. 1, Ex. 2A)

A *K. marxianus* colony corresponding to CD607 (see Ex. 1A) is cultured and 20 ml of cells are spun down. Plasmid pMM22 is digested with NheI and NaeI (both of which cut into the KmCYB2 flanks on the plasmid) and the resulting fragments are used to transform *K. marxianus* strain CD607 using standard electroporation methods. Transformants are selected based on resistance to G418.

Selected transformants are screened on yeast nitrogen base (YNB)+1% lactate plates and YNB (6.7 g/L Yeast Nitrogen Base, Difco Laboratories, Sparks Md., Cat. No. 0392-15)+ 1% glucose. Transformants that show reduced growth in the lactate medium are selected. These transformants are screened using an inside-out colony PCR using primers designated as SEQ. ID. NO. 7 and SEQ. ID. NO. 8. The 5' primer is positioned on the 5' CYB2 flank outside the homology of the disruption construct and the 3' primer is positioned within the G418 cassette. Each of the selected transformants shows an insertion of the G418 cassette at the KmCYB2 locus. Genomic DNA from four of these transformants is isolated and PCR analysis of the KmCYB2 locus performed using primers designated as SEQ. ID. NO. 9 and SEQ. ID. NO 10. These primers are positioned ~500 bp up and/or downstream of the CYB2 coding region to ensure complete amplification of the locus. PCR products having an increased size relative to the native CYB2 coding region indicate the substitution of the G418 cassette for the CYB2 gene for each of these four transformants. One of these transformants is designated as strain CD936.

EXAMPLE 2C

Generation of a *K. marixanus* Mutant (CD998) with an Integrated LDH gene, Deleted PDC Gene and Deleted KmCYB2 Gene by Transforming *K. marxianus* Strain CD635 with Plasmid pMM22 (FIG. 1, Ex. 2A)

Cells of strain CD635 (Example 1A) are transformed with plasmid pMM22 in the general manner described in Example 2B. Transformants are selected based on resistance to G418.

Selected transformants are screened on YNB+1% lactate plates and YNB+1% glucose. All transformants show reduced growth in the lactate medium. These transformants are screened using an inside-out colony PCR as described in Example 2B, and 11 of the transformants are found to have an insertion of the G418 cassette at the KmCYB2 locus. Genomic DNA from four of these transformants is isolated and PCR analysis of the KmCYB2 locus performed as described in Example 2B. As before, the primers are positioned ~500 bp up and/or downstream of the KmCYB2 coding region to ensure complete amplification of the locus. PCR products having an increased size relative to the native KmCYB2 coding region indicate the substitution of the G418 cassette for the KmCYB2 gene for three of these four transformants. One of these three transformants is designated as CD998.

EXAMPLE 3A

Construction of a Plasmid (pMM28, FIG. 2) containing the KmCYB2 Gene Cassette between *K. thermotolerans* Direct Repeat Sequences The entire *K. marxianus* CYB2 (KmCYB2) gene cassette, including promoter and terminator regions, is PCR amplified from the genomic genomic DNA of a wild-type *K. marxianus* strain designated as CD21, with introduction of BamHI and SalI restriction sites, by PCR using primers identified as SEQ. ID. NO. 11 and SEQ. ID. NO. 12. The PCR product is ligated to a commercial vector designated as pUC18 (from Invitrogen Corp., Carlsbad, Calif. USA) that is digested with BamHI and SalI. The resulting plasmid is designated as pMM25.

A 705 bp sequence identified as SEQ. ID. NO. 13 is PCR-amplified from the genomic DNA of *K. thermotolerans*, with introduction of SphI and SalI restriction sites, using primers identified as SEQ. ID. NO. 14 and SEQ. ID. NO. 15. This *K. thermotolerans* sequence does not encode for any active protein. Plasmid pMM25 is digested with SphI and SalI and the *K. thermotolerans* sequence is ligated to it upstream (5') to the KmCYB2 cassette to form a plasmid designated as pMM27.

An identical *K. thermotolerans* sequence is PCR-amplified with addition of BamHI and XmaI restriction sites, using primers identified as SEQ. ID. NO. 16 and SEQ. ID. NO. 17. Plasmid pMM27 is digested with BamHI and XmaI and the K thermotolerans sequence is ligated to it downstream (3') from the KmCYB2 cassette to form a plasmid designated as pMM28 (FIG. 2). Plasmid pMM28 contains the KmCYB2 cassette flanked by *K. thermotolerans* direct repeat sequences, both oriented in the same direction.

EXAMPLE 3B

Construction of a Plasmid (pMM35, FIG. 3) containing a *S. cerevisise* MEL1 Gene Expression Cassette between Identical *K. thermotolerans* Sequences and between 5' and 3' KmCYB2 Flanking Regions A vector designated as pNC16 is obtained from the National Research Energy Laboratories in Golden, Colo. This plasmid contains the *S. cerevisiae* MEL1 gene under the control of the *S. cerevisiae* PDC1 promoter and *S. cerevisiae* GAL10 terminator. The MEL1 gene cassette is PCR-amplified with addition of BglII and SalI restriction sites using primers designated as SEQ. ID. NO. 18 and SEQ. ID. NO. 19. Plasmid pMM28 (FIG. 2, Ex. 3A) is digested with BamHI and SalI and ligated to the MEL1 cassette. This simultaneously deletes the KmCYB2 cassette of plasmid pMM28 and replaces it with the MEL1 cassette. The resulting plasmid is designated pMM31. It contains the MEL1 cassette flanked by the *K. thermotolerans* direct repeat sequences.

A ~2 kbp flanking region directly 3' of the KmCYB2 coding region is amplified with introduction of XmaI and SacI restriction sites by PCR using primers identified as SEQ. ID. NO. 20 and SEQ. ID. NO. 21 and genomic DNA as the template. The resulting fragment is ligated to XmaI/SacI-digested plasmid pMM31 to insert the 3' CYB2 flank downstream (3') of the *K. thermotolerans* direct repeat sequence that is itself downstream of the MEL1 cassette. The resulting plasmid is designated as pMM32.

A ~2 kbp flanking region directly 5' of the KmCYB2 coding region is amplified with introduction of AatII and NarI restriction sites by PCR using primers identified as SEQ. ID. NO. 22 and SEQ. ID. NO. 23 and genomic DNA as the template. The resulting fragment is ligated to AatII/NarI-digested plasmid pMM32. The resulting plasmid (designated pMM35, FIG. 3), contains, in order, the 5' KmCYB2 flanking region, a first *K. thermotolerans* direct repeat sequence, the MEL1 cassette, the second *K. thermotolerans* direct repeat sequence and the 3' KmCYB2 flanking region.

EXAMPLE 3C

Generation of a *K. marixanus* Mutant (CD1287) with a Deleted KmCYB2 Gene by Transforming a Wild-Type *K. marxianus* Strain with Plasmid pMM35

Plasmid pMM35 is digested with BsmI and NheI and used to transform cells of a wild-type *K. marxianus* strain, using standard electroporation methods. Transformants are selected for growth by plating on YNB+2% melibiose, with the addition of 32 mg/L XaGal (5-bromo-4-chloro-3-indolyl-beta-D-galactoside, LabScientific, Inc., Livingston, N.J., Cat. No. X-566). All transformants that grow on this medium are blue in color. They are subsequently streaked to melibiose plates for further analysis. The transformants are screened for homologous recombination at the KmCYB2 locus via 5' inside-out colony PCR using primers identified as SEQ. ID. NO. 7 and SEQ. ID. NO. 8. Colonies yielding a positive PCR product are twice single colony isolated on YNB+2% melibiose and 32 mg/L XaGal to eliminate background contamination. Genomic DNA is obtained from these strains.

The entire KmCYB2 locus is amplified via PCR using primers identified as SEQ. ID. NO. 24 and SEQ. ID. NO. 25. Four colonies give a PCR product as expected for a homologous recombination at KmCYB2 resulting in an insertion of the MEL1 gene cassette at the KmCYB2 locus. One of these colonies is designated CD1286.

Strain CD1286 is streaked on a non-selective medium for two rounds and plated for single colony isolates, to screen for a loopout of the MEL1 cassette. Three out of approximately 1300 colonies appear to be white, indicating the absence of the MEL1 gene. Genomic DNA is obtained from these three colonies, and PCR of the entire KmCYB2 locus is performed, again using primers identified as SEQ. ID. NO. 24 and SEQ. ID. NO. 25. AR three colonies give the expected PCR product for a loopout event, indicating that the MEL1 cassette has become deleted from the cell's genome. One of these strains is designated CD1287.

EXAMPLE 4A

Construction of a Plasmid (pMM38, FIG. 5) containing the 5' KmPDC1 Flanking Region, an *L. helveticus* LDH Gene Expression Cassette, a KmCYB2 Gene Expression Cassette Flanked by *K. thermotolerans* Direct Repeat Sequences, and the 3' KmPDC1 Flanking Region The TEF2 promoter region from a wild-type *K. marxianus* strain is amplified with the addition of KpnI/XbaI sites using primers identified as SEQ. ID. NO. 26 and SEQ. ID. NO. 26, using genomic DNA as the template. The subsequent ligation of this product into a plasmid designated pBH76 (FIG. 4) yields a plasmid designated as pMM36. Plasmid pMM36 contains, in order, the 5' KmPDC1 flanking region, the KmTEF2 promoter, the LhLDH gene and the ScGAL10 terminator. The 3' KmPDC1 flanking region is then amplified by PCR with addition of XmaI/PciI sites using primers identified as SEQ. ID. NO. 28 and SEQ. ID. NO. 29 and genomic DNA as the template. This amplicon is ligated into plasmid pMM28 (FIG. 2, Ex. 3A) by cutting with XmaI/PciI to yield a plasmid designated pMM37. The KmPDC1 region and LhLDH expression cassette from plasmid pMM36 are amplified with the addition of NarI/NdeI sites using primers designated as SEQ. ID. NO 30 and SEQ. ID. NO. 31, and this region is ligated into NarI/NdeI-digested pMM37 to produce plasmid pMM38 (FIG. 5). Plasmid pMM38 is designed for targeted insertion of LhLDH and KmCYB2 gene expression cassettes at the *K. marxianus* PDC1 locus.

EXAMPLE 4B

Generation of a *K. marxianus* Mutant (CD 1300) having an Exogenous LDH Gene, a Deleted PDC Gene and Looped Out CYB2 Gene, by Transforming Strain CD1287 with Plasmid pMM38 (FIG. 5, Ex. 4A)

Plasmid pMM38 is digested with NdeI and used to transform strain CD 1287, using standard electroporation methods. Transformants are selected for growth on YNB+2% lactate plates. Transformants growing on the lactate plates are streaked to lactate plates and to YPD plates. These transformants are screened for a homologous recombination at the PDC1 locus via 3' inside-out PCR using primers identified as SEQ. ID. NO. 32 and SEQ. ID. NO. 33. Transformants yielding a PCR product of the expected size (2251 bp) are streaked for single colony isolation. Genomic DNA of three single colony isolates from each positive transformant is obtained and the PDC1 locus is amplified via PCR using primers identified as SEQ. ID. NO. 34 and 35. Isolates giving the expected PCR product (8453 bp vs. 3730 bp for the wild-type PDC locus, indicating the loss of the PDC gene and integration of the LDH gene) are then tested for the Pdc-phenotype by evaluating whether they produce ethanol. One of the strains that does not produce ethanol is designated strain CD1298. Strain CD1298 contains a deleted PDC gene, the exogenous LDH gene cassette, and the CYB2 gene cassette from plasmid pMM38.

Strain CD1298 is streaked onto non-selective YPD media for three rounds and a slurry of cells are plated onto PDA+7.5 g/L glycolic acid plates. After 72 hours at 30° C., colonies are picked and screened via colony PCR for a loopout of the KmCYB2 gene, using primers identified as SEQ. ID. NO. 36 and 37. Four colonies give the correct product size for a loopout of the CYB2 gene (1109 bp vs 5129 bp for the product containing the CYB2 cassette). Single colonies are isolated from each of these four strains. Genomic DNA is obtained from each of these single colonies and the PDC1 locus is amplified via PCR using primers identified as SEQ. ID. NO. 38 and 36. Two strains yield a PCR product of the size expected for a loopout of the CYB2 cassette (3249 bp vs 7269 bp for the product containing the CYB2 cassette and 2546 for the wild-type PCR product). One of these two strains is designated as strain CD1300.

EXAMPLE 5A

Microaerobic Shake Flask Characterizations of Strains CD635 (Ex. 1A), CD853 (Ex. 1A) and CD998 (Ex. 2C)

Strains CD635, CD853 and CD998 are separately cultivated at low density (0.05-0.10 OD600) and allowing the culture to produce fermentation products while growing. Fifty mL of media (YP+60 g/L dextrose) is pipetted into a 250 mL baffled shake flask and the media is inoculated with the required amount of biomass. The flask is then incubated at 30° C. and orbitally agitated at 70 rpm for ~92 hours with samples being taken (~every 24 hours) during the course of the experiment to test for glucose consumption, fermentation product accumulation, as well as biomass growth.

After 92 hours of cultivation, strain CD635 (not an example of this invention), has consumed 17.6 g/L of glucose and produced 11.4 g/L lactate. In the same time period, strain CD853 consumes 26.9 g/L of glucose and produces 23.3 g/L lactate, slightly more than double that produced by strain CD635. Strain CD998 consumes 21.9 g/L glucose and produces 18.5 g/L lactate, more than 60% more than strain CD635. Yield to lactate is ~65% for strain CD635, whereas yields for strains CD835 and CD998 are ~86.6% and 84.5%, respectively.

EXAMPLE 5B

Evaluation of Resistance to Glycolic Acid for Strains CD635 (Ex. 1A), CD853 (Ex. 1A) and CD998 (Ex. 2C)

Duplicate PDA plates are made containing concentrations between 5 g/L through 25 g/L of glycolic acid. Control plates containing no glycolic acid are also prepared. A dilution series of strains CD635, CD853 and CD998 is prepared, and 5 μL of each dilution of the dilution series is spotted onto each of the above plates. The inoculated plates are cultured at 30° C. for three days. Comparative strain CD635 grows on plates containing glycolic acid up to a concentration of 15 g/L, but fails to grow on any of the glycolic acid-containing plates with higher concentration. Strain CD853 exhibits ability to grow on glycolic acid plates containing up to 25 g/L glycolic acid. Strain CD998 can grow on plates containing up to 22.5 g/L glycolic acid. These tests indicate that glycolic acid can be used as a selective medium for mutant strains having a non-functional CYB2 gene.

EXAMPLE 6

Microaerobic Shake Flask Characterizations of Comparative Strain CD607 (Ex. 1A), Strain CD936 (Ex. 2B) and Strain CD1300 (Ex. 3C)

Strains CD607, CD936 and CD1300 are separately cultivated under the conditions described in Example 5A. After 93 hours of cultivation, comparative strain CD607 has consumed 16.5 g/kg of glucose and produces 10.8 g/kg lactate. In the same time period, strain CD936 consumes 21.6 g/kg of glucose and produces 19.3 g/kg lactate, slightly less than double that produced by strain CD607. Strain CD1300 consumes 29.9 g/kg glucose and produces 24.6 g/kg lactate, more than 125% more than strain CD607. Yield to lactate is 65.5% for strain CD607, whereas yields for strains CD936 and CD1300 are 89.4% and 82.3%, respectively. The strain CD607 also produces 2.02 g/kg pyruvic acid in this time frame, whereas CD936 and CD1300 produce 0.68 g/kg and 0.83 g/kg pyruvic acid respectively. Also in this time frame, CD607 produces 0.67 g/kg acetic acid in comparison to no acetic acid production for either CD936 or CD 1300.

Growth is also monitored during this experiment. After 93 hours, comparative strain CD607 has grown to an OD600 of about 5.7, whereas strains CD936 and CD1300 have grown to an OD600 of about 7.5 and 3.2, respectively. The much lower growth of strain CD 1300 indicates that the specific productivity of this strain is much higher than that of comparative strain CD607 and strain CD936.

EXAMPLE 7A

Cloning of *I. orientalis* PGK (IoPGK1) Promoter Region; Construction of a Plasmid (pMI318, FIG. 6) having the *E. coli* Hygromycin Gene under the Control of the IoPGK1 Promoter and the *S. cerevisiae* GAL10 Terminator A 920 bp probe fragment of the *C. sonorensis* PGK1 gene is obtained from the genomic DNA of *C. sonorensis* in the same manner as described in Example 22 of WO 02/042471, using primers identified as SEQ. ID. NO. 39 and SEQ. ID. NO. 40. Genomic DNA is isolated from a growing *I. orientalis* strain and resuspended in 10 mM Tris-HCl+1 mM EDTA (pH 8) (TE). The *I. orientalis* genomic DNA is cut with HindIII, and a Southern blot is prepared and hybridized using standard methods with the *C. sonorensis* PGK1 gene as a probe. Fragments of ~2 kbp size are isolated from agarose gel and cloned into a HindIII-cut plasmid. Colony hybridization of the *E. coli* transformants with the PGK1 probe result in isolation of a HindIII fragment containing most of the *I. orientalis* PGK1 (IoPGK1) protein coding sequences but no promoter sequences, as verified by sequencing.

Genomic fragments containing the IoPGK1 promoter region are obtained with ligation-mediated PCR amplification (Mueller, P. R. and Wold, B. 1989, "In vivo footprinting of a muscle specific enhancer by ligation mediated PCR." Science 246:780-786). A mixture of a linker identified as SEQ. ID. NO. 41 and a linker identified as SEQ. ID. NO. 42 is ligated to HaeIII-digested *I. orientalis* genomic DNA with T4 DNA ligase (New England BioLabs). Samples of the ligation mixtures are used as templates for 50 μl PCR reactions containing 0.1 μM of a primer identified as SEQ. ID. NO. 43 and 1 μM of a primer identified as SEQ. ID. NO. 44. The reaction mixture is heated at 94° C. for 3 minutes after 2 U of Dynazyme EXT is added. The reactions are cycled 30 times as follows: 1 minute at 94° C., 2 minutes at 68° C. and 2 minutes at 72° C., with a final extension of 10 minutes at 72° C. A diluted sample of this first PCR-amplification is used as the template in a nested PCR reaction (50 μl) containing 0.05 μM of a primer identified as SEQ. ID. NO. 45 and 0.5 μM of a primer identified as SEQ. ID. NO. 46. The reaction mixture is heated at 94° C. for 3 minutes after 2 U of Dynazyme EXT is added. The reactions are then cycled 30 times as follows: 1 minute at 94° C., 2 minutes at 67° C. and 2 minutes at 72° C., with a final extension of 10 minutes at 72° C.

A ~600 bp PCR fragment is isolated and sequenced. Nested primers identified as SEQ. ID. NO. 47 and SEQ. ID. NO. 48 are designed and used in a ligation-mediated PCR amplification together with oligonucleotides identified as SEQ. ID. NO. 49 and SEQ. ID. NO. 50 similarly as above except that SphI-digested *I. orientalis* DNA is used and the PCR is carried out using an annealing temperature of 65° C.

The *I. orientalis* PGK1 promoter is PCR amplified using primers identified as SEQ. ID. NO. 51 and SEQ. ID. NO. 52 and the *I. orientalis* genomic DNA as the template. The fragment is filled in using the Klenow enzyme and then cut with XbaI. A 633 bp fragment is gel isolated and ligated to a 4428 bp fragment obtained by digesting a plasmid designated as pMI270 (described in FIG. 4 of WO 03/049525) with XhoI, filling the fragment in using the Klenow enzyme and 0.1 mM dNTP, and digesting with XbaI. Plasmid pMI270 contains the *E. coli* hygromycin gene linked to a *C. sonorensis* PGK1 promoter and a *S. cerevisiae* GAL10 terminator. The resulting plasmid is designated pMI318 (FIG. 6). Plasmid pMI318 contains the *E. coli* hygromycin gene under the control of the *I. orientalis* PGK1 promoter and the *S. cerevisiae* GAL10 terminator.

EXAMPLE 7B

Construction of a Plasmid (pMI321, FIG. 7) containing the Hygromycin Gene under the Control of the IoPGK1 Promoter and the *S. cerevisiae* GAL10 Terminator, and the *L. helveticus* LDH Gene under the Control of the IoPGK1 Promoter and *S. cerevisiae* CYC1 Terminator The *I. orientalis* PGK1 promoter from Example 7A is PCR amplified using primers identified as SEQ. ID. NO. 53 and SEQ. ID. NO. 54 and the *I. orientalis* genomic DNA as the template. The fragment is filled in using the Klenow enzyme and 0.1 mM dNTP, and then cut with NcoI. A 633 bp fragment is gel isolated.

Plasmid pVR1 (described in WO 03/102152 FIG. 7) contains the *L. helveticus* LDH gene under the control of the *S. cerevisiae* TEF1 promoter and the *S. cerevisiae* CYC1 terminator. Plasmid pVR1 is digested with XhoI, filled in using the Klenow enzyme, and cut with NcoI. A 7386 bp fragment from plasmid pVR1 is ligated to the 633 bp IoPGK1 promoter fragment. The resulting plasmid is designated pMI320. Plasmid pMI320 contains the *L. helveticus* LDH gene under the control of the IoPGK1 promoter and *S. cerevisiae* CYC1 terminator.

Plasmids pMI318 (FIG. 6, Ex. 7A) and pMI320 are digested with ApaI and NotI. A 5008 bp fragment from plasmid pMI318 is ligated to a 1995 bp fragment from plasmid pMI320 to form plasmid pMI321 (FIG. 7).

The hygromycin gene (and its terminator) is positioned on plasmid pMI321 between two copies of the IoPGK1 promoter, which serve as direct repeat sequences. This construct can permit a cell transformed with plasmid pMI321 to engage in a homologous recombination to "loop out" the hygromycin gene and terminator, together with one copy of the IoPGK1 promoter.

EXAMPLE 7C

Cloning of *L. orientalis* PDC (IoPDC1A) Promoter Region; Construction of a Plasmid (pMI355, FIG. 8) having the *E. coli* Hygromycin Gene under the Control of the IoPGK1 Promoter and the *S. cerevisiae* GAL10 Terminator, the *L. helveticus* LDH Gene under the Control of the IoPGK1 Promoter and *S. cerevisiae* CYC1 Terminator, and the IoPDC1A 5' Flanking Region A genomic library of the wild-type *I. orientalis* strain ATCC PTA-6658 is constructed into the SuperCos1 (Stratagene) cosmid vector according to instructions provided by the manufacturer. PDC-like sequences are amplified by PCR from the genomic DNA of the strain with primers designated as SEQ. ID. NO. 55 and SEQ. ID. NO. 56. A 700 bp fragment of a PDC gene is amplified. The genomic library is screened using hybridization techniques with labeled PCR fragments as probes as described in WO 03/049525 and cosmid clones containing the PDC gene are isolated and sequenced. The *I. orientalis* PDC1A 5' region from 1000 bp to 167 bp upstream of the start of the open reading frame is PCR amplified using primers identified as SEQ. ID. NO. 57 and SEQ. ID. NO. 58 and the *I. orientalis* PDC cosmid DNA as the template. The fragment is cut with SalI and SacI. An 836 bp fragment is gel isolated and ligated to a 6992 bp fragment obtained by digesting plasmid pMI321 (FIG. 7, Example 7B) with SalI and SacI. The resulting plasmid is named pMI355 (FIG. 8).

EXAMPLE 7D

Cloning of *I. orientalis* PDC (IoPDC1A) Terminator Region; Construction of Plasmids (pMI356 (FIG. 9) and pMI357) and having the IoPDC1A 5' Flanking Region, the *E. coli* Hygromycin Gene under the Control of the IoPGK1 Promoter and the *S. cerevisiae* GAL10 Terminator, the *L. helveticus* LDH Gene under the Control of the IoPGK1 Promoter and *S. cerevisiae* CYC1 Terminator, and the IoPDC1A 3' Flanking Region The *I. orientalis* PDC 3' region corresponding to sequences from 233 bp to 872 bp downstream of the PDC translation stop codon is PCR amplified using primers identified as SEQ. ID. NO. 59 and SEQ. ID. NO. 60 and the *I. orientalis* PDC1A cosmid DNA (Example 7C) as the template. The fragment is cut with ApaI and SmaI. A 630 bp fragment is gel isolated and ligated to a 7809 bp fragment obtained by digesting plasmid pMI355 (FIG. 8, Ex. 7C) with ApaI and SmaI. The resulting plasmid is named pMI356 (FIG. 9). It contains the hygromycin and LDH cassettes from plasmid pMI355 between the 5' flank and a portion of the 3' flank of the IoPDC1A gene.

Plasmid pMI357 is made in a similar way, except that it differs from plasmid pMI356 with respect to the portion of the 3' IoPDC1A flank that is present. This regions corresponds to the sequence 5 bp upstream and 216 bp downstream of the PDC translation stop codon.

EXAMPLE 7E

Generation of an *L. orientalis* Mutant (CD1184) with Deleted IoPDC1A and IoPDC1B Genes and Integrated LhLDH Gene in One Step by Transforming Wild-Type *L. orientalis* Strain with Plasmid pMI356 (FIG. 9, Ex. 7D)

Wild-type *I. orientalis* strain ATCC PTA-6658 is transformed with plasmid pMI356 using standard methods. Transformed strains that grow on hygromycin plates are cultured. A transformant that does not produce ethanol is selected for Southern analysis, which confirms the deletion of both the IoPDC1A and IoPDC1B genes and insertion of at least one copy of the LhLDH gene. This strain is designated CD1184.

EXAMPLE 7F

Construction of Plasmid pMI433 (FIG. 10) containing the IoPDC1A 5' Flanking Region, the ScMEL5 Gene under the Control of the IoPGK1 Promoter, the *L. helveticus* LDH Gene under the Control of the IoPGK1 Promoter and ScCYC1 Terminator, and the IoPDC1A 3' Flanking Region The *I. orientalis* PGK1 promoter is PCR amplified using primers identified as SEQ. ID. NO. 61 and SEQ. ID. NO. 62 and the *I. orientalis* genomic DNA as the template. The fragment is filled in using the Klenow enzyme and 0.1 mm dNTP, and then cut with SphI. A 669 bp fragment is gel isolated. A plasmid designated as pMI233 (described in FIG. 23C of WO 03/049525) is cut with XhoI. The fragment is filled in with the Klenow enzyme and cut with SphI. The 4534 bp and the 669 bp fragments are ligated and the resulting plasmid is named pMI319. Plasmid pMI319 contains the *S. cerevisiae* MEL5 (ScMEL5) gene and the IoPGK1 promoter region.

Plasmid pMI319 plasmid is cut with ApaI, made blunt ended with T4 polymerase, and cut with NotI. A 2317 bp fragment is gel isolated. It is ligated to a 6498 bp fragment obtained by digesting plasmid pMI357 (Example 7D) with SalI, making it blunt ended with the Klenow enzyme and then cutting with NotI. The resulting plasmid contains the ScMEL5 gene (with its native terminator) in place of the hygromycin gene of plasmid pMI357. The resulting plasmid is designated pMI433 (FIG. 10).

EXAMPLE 7G

Construction of Plasmids pMI449 (FIG. 11) and pMI454 (FIG. 12) containing *L. orientalis* CYB2 5' Flanking Region, ScMEL5 Gene Cassette between *K. thermotolerans* Direct Repeat Sequences and *L. orientalis* CYB2 3' Flanking Region Plasmid pMM28 (FIG. 2, Ex. 3A) is digested with BamHI, filled in with the Klenow enzyme, and digested with SalI. The 4077 bp fragment so obtained is ligated to a 2317 bp NotI (filled in with Klenow enzyme)-SalI fragment of pMI433 (FIG. 10, Ex. 7F). The resulting plasmid is designated pMI445.

The 3' flanking region of the *I. orientalis* L-lactate:ferricytochrome c oxidoreductase (IoCYB2A) gene (corresponding to sequences from 90 to 676 bp downstream of the predicted open reading frame) is amplified by PCR using primers identified as SEQ. ID. NO. 63 and SEQ. ID. NO. 64 using a CYB2-2 cosmid clone as a template. The PCR product is digested with SacI and SmaI and the 607 bp fragment is ligated to the 6386 bp SacI-SmaI fragment of plasmid pMI445. The resulting plasmid is designated pMI448.

The IoCYB2A 5' flanking region (corresponding to sequences from 913 to 487 bp upstream of the predicted open reading frame) is amplified by PCR using primers identified as SEQ. ID. NO. 65 and SEQ. ID. NO. 66, again using the CYB2-2 cosmid clone as a template. The PCR product is digested with SphI and the 454 bp fragment is ligated to the 6993 bp SphI fragment obtained by partially digesting pMI448. The resulting plasmid is designated pMI449 (FIG. 11).

The IoCYB2A 5' flanking region (corresponding to sequences from 466 to 7 bp upstream of the predicted open reading frame) is amplified by PCR using primers identified as SEQ. ID. NO. 67 and SEQ. ID. NO. 68, once again using the CYB2-2 cosmid clone as the template. The PCR product is digested with SphI and the 493 bp fragment was ligated to the 6993 bp SphI fragment obtained by partially digesting plasmid pMI448. The resulting plasmid is designated pMI453.

The IoCYB2A 3' flanking region (corresponding to sequences from 402 bp upstream to 77 bp downstream of the predicted stop codon) is amplified by PCR using primers identified as SEQ. ID. NO. 69 and SEQ. ID. NO. 70 using the CYB2-2 cosmid as a template. The PCR product is digested with ApaI and SmaI and the 506 bp fragment is ligated to the 6886 bp ApaI-SmaI fragment of plasmid pMI453. The resulting plasmid is designated pMI454 (FIG. 12).

EXAMPLE 7H

Generation of *I. orientalis* Mutant Strain (CD1496) by Successively Transforming Strain CD1184 (Ex. 7E) with Plasmids pMI449 and pMI454, Followed by Mutagenesis Strain CD1184 is transformed with plasmid pMI449 using the lithium acetate method and transformants (blue colonies) are selected based on melibiase activity on YPD X-α-gal plates. The replacement of the IoCYB2A gene of strain CD1184 with the transformed DNA is confirmed by colony PCR and Southern analysis in some of the transformants. The MEL5 marker is looped out from one of those transformants via a homologous recombination event through the *K. thermotolerans* repeat sequences, as confirmed by Southern analysis. The second CYB2A allele is deleted from this transformant using plasmid pMI454. Transformants are analyzed by colony PCR for the absence of a 1000 bp CYB2A specific PCR product. The MEL5 marker from plasmid pMI454 is looped out of a transformant having a deletion of the second CYB2A allele via recombination as before. This transformant is designated strain CD1436.

Strain CD1436 is subjected to EMS mutagenesis using the conditions set forth in Example 1A, except the exposure conditions are 8 uL for 1 hour. Mutagenized cells are allowed to recover for 6 hours on YPD and then plated onto PDA+35 g/L lactic acid plates and incubated for one week at 30° C. A strain that produces more lactate and less glycerol than strain CD1436 is designated as strain CD1496. Strain CD1496 has a deletion of both PDC1 alleles (with replacement by a functional L-LDH gene cassette, and a deletion of each of its two native IoCYB2A alleles).

EXAMPLE 7I

Shake Flask Fermentations using Strains CD1184, CD1436 and CD1496

Strains CD1184 and CD1436 are evaluated in microaerobic shake flask fermentations in the general manner described in Example 5A, except the starting dextrose concentration is 100 g/L and agitation is at 100 rpm. Each strain stops consuming glucose after about 80 hours of production. After 144 hours of cultivation, final lactate titer is lactate production is about 60 g/kg for strain CD 1184 and 53 g/kg for strain CD1436. Lactate yield is about 88% for strain CD1184 and 86% for strain CD1436. Glycerol yield is about 5.5% for strain CD1184 and 8.5% for strain CD1436.

Strains CD 1436 and CD 1496 are similarly evaluated in duplicate microaerobic cultivations. After 144 hours of cultivation, final lactate titer is lactate production is about 58 g/kg for strain CD1436 and 65 g/kg for strain CD1496. Lactate yield is about 68% for each strain. Glycerol yield is about 11% for strain CD1436 and only about 8% for strain CD1496.

EXAMPLE 7J pH 3 Fermentations of Strains CD1436 (Example 7H) and CD1496 (Example 7H)

Strains CD1436 and CD1496 are used in separate fermentations buffered to a pH of 3.0. In each instance the cells are inoculated to a 5 L Braun-B fermenter with a working volume of 3 L. The fermentation broth contains 110 g/L of dextrose at the beginning of the fermentation. Potassium hydroxide is added as needed to maintain the pH of the fermentation broth at 3.0. Fermentation temperature is 30° C. Oxygen is added to maintain a oxygen uptake rate of 5-6 mmol/L-hr.

Strain CD1436 produces lactate at a rate of 0.77 g/l-hr, to a final yield of 69%. Strain CD1496 produces lactate at a rate of 0.83 g/l-hr, to a final yield of 64%. Stains CD1436 and CD1496 produce 0.8 and 0.0 g/L pyruvate, respectively. They produce 18 and 23 g/L glycerol, respectively. Neither produces measurable acetate.

EXAMPLE 7K pH 3 Fermentations of Strain CD1436 (Ex. 7H) and its Parent Strain CD1184 (Ex. 7E)

Strain CD1436 and its parent strain CD1184 are used in separate fermentations buffered to a pH of 3.0. In each instance the cells are inoculated to a 5 L Braun-B fermenter with a working volume of 3 L. The fermentation broth contains 130 g/l of dextrose at the beginning of the fermentation. Potassium hydroxide is added as needed to maintain the pH of the fermentation broth at 3.0. Fermentation temperature is 30° C. Oxygen is added to maintain an oxygen uptake rate of 2 mmol/L-hr.

Strain CD1436 produces a 66 g/L of lactate after about 160 hours of cultivation, whereas strain CD1184 produces only 56 g/L of lactate. Strain CD1436 also produces lactic at a higher volumetric rate than strain CD1184 (0.43 vs. 0.35 g/l-h). In addition, strain CD1436 accumulates no acetate or pyruvate whereas strain CD1184 produces about 1 g/L of pyruvate and 3 g/L of acetate. Strain CD 1436 has an overall yield of lactic on glucose of about 67% vs. 69% for its parent. The comparable yields are obtained because strain CD1436 produces more glycerol than strain CD1184.

EXAMPLE 8A

Deletion of DLD1 Gene from a *K. marxianus* Strain Containing an Exongenous D-LDH Gene Cassette The 3' downstream locus of the DLD1 gene of a wild-type *K. marxianus* strain is amplified with addition of NarI/SalI restriction sites using primers identified as SEQ. ID. NO. 71 and SEQ. ID. NO. 72 and genomic DNA as the template. The cloned region is ligated to plasmid pMM31 (Ex. 3B) to form plasmid pMM44 (FIG. 13). The 5' downstream locus of the DLD1 gene of a wild-type *K. marxianus* strain is amplified with addition of XmaI/NcoI restriction sites using primers identified as SEQ. ID. NO. 73 and SEQ. ID. NO. 74 and genomic DNA as the template. The cloned region is ligated to plasmid pMM31 (Ex. 3B) to form plasmid pMM45 (FIG. 14).

A fragment is amplified from plasmid pMM44 using primers identified as SEQ. ID. NO. 71 and SEQ. ID. NO. 75. Another fragment is amplified from plasmid pMM45 using primers identified as SEQ. ID. NO. 74 and SEQ. ID. NO. 76. The amplified products (~2.8 kbp from pMM44 and ~2.5 kbp from pMM45) are gel purified and used to transform a *K. marxianus* strain containing an exogenous D-LDH gene cassette (and having an intact PDC gene), which is prepared according to methods similar to those described in WO 03/102152. Following a 4 hour recovery, cells are plated on YNB 2% melibiose+32 mg/L XaGal plates.

Transformants are screened for a homologous recombination of the transformed DNA at the DLD1 locus via inside-out colony PCR using primers identified as SEQ. ID. NO. 77 and SEQ. ID. NO. 78. The primers are homologous to a region upstream of the cloned 5' region and to the coding region of the selection marker ScMEL1, respectively. Three of 32 transformants screened give the expected PCR product of 1.8 kb and are streaked for single colony isolates.

The entire DLD1 locus is amplified from genomic DNA from single colony isolates of two of the three positive transformants using primers identified as SEQ. ID. NO. 74 and SEQ. ID. NO. 77. All single colonies yield the expected product for a knockout of the DLD1 gene. One of these strains is identified as strain CD 1603.

Strain CD1603 and the parent strain were separately streaked to YNB plates containing 2% D-Lactic acid as the sole carbon source. The parent strain grows well in this medium, but strain CD 1603 shows negligible growth.

Strain CD1603 and the parent strain are separately cultivated in the general manner described in Example 5A. Lactic acid and byproduct production are measured via HPLC throughout the cultivations. Lactic acid production is improved in strain CD1603 compared to the parent strain. Both lactic production rate and lactic titer are higher in strain CD1603 than in the parent strain.

EXAMPLE 8B pH 3 Fermentations of Strain CD1603 (Example 8A) and its Parent Strain Strains CD1603 and its parent are used in separate fermentations buffered to a pH of 3.0. In each instance the cells are inoculated to a 5 L Braun-B fermenter with a working volume of 3 L. The fermentation broth contains 90 g/L of dextrose at the beginning of the fermentation. Potassium hydroxide is added as needed to maintain the pH of the fermentation broth at 3.0. Fermentation temperature is 30° C. Oxygen is added to maintain an oxygen uptake rate of 5-6 mmol/L-hr.

Strain CD1603 produces lactate at a rate of 0.58 g/l-hr, to a final yield of 69%. It produces pyruvate at a yield of 0.8% and glycerol at a yield of 7.3%. The parent strain produces lactate at a rate of only 0.09 g/l-hr, to a final yield of 68%. The pyruvate and glycerol yields of the parent strain are 21% and 6.9%, respectively. These values indicate that the parent strain consumes lactate as it forms, converting it to pyruvate. In addition, the parent strain produces a yield of 15% acetate.

EXAMPLE 9

Production of *S. bulderi* Yeast Cells having an Exogenous LhLDH Gene and an Exogenous G418 Gene Cassette

*S. bulderi* is a yeast that, as a native strain, lacks ability to grow on lactate as the sole carbon source. Primers identified as SEQ. ID. NO. 85 and SEQ. ID. NO. 86 are used for walking in conjunction with AP1 from the Universal Gene Walking kit (BD BioSciences Clontech, Pal Alto, Calif., Catalog No. K1807-1) to elucidate a ~1 kbp sequence upstream from the *S. bulderi* TEF1 gene. A 850 bp sequence of the that upstream sequence is cloned immediately upstream of an LhLDH gene, using SacI/XbaI cloning sites on primers identified as SEQ. ID. NO. 87 and SEQ. ID. NO. 88, to produce a plasmid designated as pCM149 (FIG. 15). Plasmid pCM149 contains, in order, the SbTEF1 promoter, the LhLDH gene, a *Saccharomyces exigus* PGI terminator, a G418 gene cassette under the control of the ScPDC1 promoter and the ScGal10 terminator. The SePG1 terminator is obtained by amplifying *S. exiguus* genomic DNA with primers identified as SEQ. ID. NO. 89 and SEQ. ID. NO. 90. The G418 gene cassette is described in Example 1A (FIG. 4) of WO03/102152.

Cells of a wild-type *S. bulderi* (ATCC strain MYA-403) are transformed with plasmid pCM149 using standard lithium acetate methods. Transformants are plated onto YPD+300 mg/L G418, and three transformants produce faint purple halos using a LASSO assay, which indicates that these strains are producing lactic acid. These three strains are separately inoculated onto YPD shake flasks, and all three are found to produce lactic acid. All three strains produce from 5-7 g/L lactic acid after about 24 hours of cultivation. The parent wild-type strain does not produce any lactic acid.

We claim:

1. A genetically modified yeast cell having (a) at least one functional exogenous lactate dehydrogenase (LDH) gene integrated into its genome and (b) a deletion or disruption of at least one native L- or D-lactate:ferricytochrome c oxidoreductase gene.

2. The genetically modified yeast cell of claim 1 having (a) a deletion or disruption of at least one native L-lactate:ferricytochrome c oxidoreductase gene and (b) at least one functional exogenous L-lactate dehydrogenase gene integrated into its genome.

3. The genetically modified yeast cell of claim 2, which is a cell of the genera *Candida, Saccharomyces, Shizosaccharomyes, Kluyveromyces, Pichia, Issachenkia* or *Hansenula*.

4. The genetically modified yeast cell of claim 2, which is a cell of the species *K. marxianus, S. cerevisiae, C. sonorensis, S. bulderi* or *I. orientalis*.

5. The genetically modified yeast cell of claim 2 further having a deletion or disruption of at least one native pyruvate decarboxylase gene.

6. The genetically modified yeast cell of claim 2 wherein the deleted or disrupted L-lactate:ferricytochrome c oxidoreductase gene is a gene having a sequence identified as SEQ ID NO: 1, SEQ ID NO: 79 or SEQ ID NO: 81.

7. The genetically modified yeast cell of claim 2 wherein the deleted or disrupted L-lactate:ferricytochrome c oxidoreductase gene encodes for an enzyme having an amino acid sequence identified as SEQ ID NO: 2 SEQ ID NO: 80 or SEQ ID NO: 82.

* * * * *